(12) United States Patent
Shen et al.

(10) Patent No.: US 7,785,887 B2
(45) Date of Patent: Aug. 31, 2010

(54) ADENOVIRUS E1B-55K SINGLE AMINO ACID MUTANTS AND METHODS OF USE

(75) Inventors: Yuqiao Shen, Richmond, CA (US); Julie Nye, Berkeley, CA (US); Terry Hermiston, Corte Madera, CA (US)

(73) Assignee: Onyx Pharmaceuticals, Inc., Emeryville, CA (US)

( * ) Notice: Subject to any disclaimer, the term of this patent is extended or adjusted under 35 U.S.C. 154(b) by 1447 days.

(21) Appl. No.: 10/669,768

(22) Filed: Sep. 24, 2003

(65) Prior Publication Data

US 2005/0053581 A1     Mar. 10, 2005

Related U.S. Application Data

(62) Division of application No. 09/918,696, filed on Jul. 30, 2001, now Pat. No. 6,635,244.

(60) Provisional application No. 60/222,887, filed on Aug. 3, 2000.

(51) Int. Cl.
C12N 15/861 (2006.01)
C12N 15/00 (2006.01)
A01N 63/00 (2006.01)
A61K 48/00 (2006.01)

(52) U.S. Cl. ............ 435/456; 424/93.1; 424/93.2; 424/93.6; 435/69.1; 435/320.1

(58) Field of Classification Search ............ None
See application file for complete search history.

(56) References Cited

U.S. PATENT DOCUMENTS 5,677,178 A    10/1997  McCormick 6,080,578 A     6/2000  Bischoff et al.
6,635,244 B2   10/2003  Shen et al.

OTHER PUBLICATIONS

Verma, I.M. and Somia, N. Gene Therapy-promises, problems and prospects, Sep. 1997, Nature, vol. 369, pp. 239-242.*
Russell, Replicating Vecotrs for Gene Therapy of Cancer: Risks, Limitations and Prospects, European J Cancer, vol. 30A, pp. 1165-1171, 1994.*
Kim, D, Replication-selective oncolytic adenoviruses: virotherapy aimed at genetic targets in cancer, Oncogene, 2000, vol. 19, pp. 6660-6669.*
Cheng, et al., 1990, "Domains Required for in Vitro Associated between the Cellular p53 and the Adenovirus 2 E1B 55K Proteins.", Virology, 179:806:814.
Harda, et al., 1999, "p53-Independent and -Dependent Requirements for E1B-55K in Adenovirus Type 5 Replication." Journal of Virology, 73(7):5333-5344.
Shen, et al., 2001, "Analyses of Single-Amino Acid Substitution Mutants of Adenovirus Type 5 E1B-55K Protein." Journal of Virology, 75(9):4297-4307.
Yew, et al., 1990, Dissection of Functional Domains in the Adenovirus 2 Early 1B 55K Polypeptide by Suppressor—Linker Insertional Mutagenesis., Virology, 179:795-805.

* cited by examiner

*Primary Examiner*—Maria Marvich
(74) *Attorney, Agent, or Firm*—Gary R. Fabian; Gregory J. Giotta

(57) ABSTRACT

Adenoviral mutants are described that have single amino acid mutations in the E1B-55K protein which mutations effect the p53 binding/inactivation and the late functions of the E1B-55K protein in a manner that enhances the efficacy of such viruses for treating cancer when compared to adenoviral mutants that have the E1B-55K region deleted.

15 Claims, 6 Drawing Sheets
(1 of 6 Drawing Sheet(s) Filed in Color)

SEQUENCE LISTING

<160> NUMBER OF SEQ ID NOS: 52

<210> SEQ ID NO 1
<211> LENGTH: 30
<212> TYPE: DNA
<213> ORGANISM: Artificial Sequence
<220> FEATURE:
<223> OTHER INFORMATION: ONYX-051

<400> SEQUENCE: 1
gttattatga atgtagcgtt tactggcccc                                     30

<210> SEQ ID NO 2
<211> LENGTH: 30
<212> TYPE: DNA
<213> ORGANISM: Artificial Sequence
<220> FEATURE:
<223> OTHER INFORMATION: ONYX-051; R240 MUTATION

<400> SEQUENCE: 2
ggggccagta aacgctacat tcataataac                                     30

<210> SEQ ID NO 3
<211> LENGTH: 33
<212> TYPE: DNA
<213> ORGANISM: Artificial Sequence
<220> FEATURE:
<223> OTHER INFORMATION: ONYX-052

<400> SEQUENCE: 3
gttttcctgg ccaatgccaa ccttatccta cac                                 33

<210> SEQ ID NO 4
<211> LENGTH: 33
<212> TYPE: DNA
<213> ORGANISM: Artificial Sequence
<220> FEATURE:
<223> OTHER INFORMATION: ONYX-052; T255A MUTATION

<400> SEQUENCE: 4
gtgtaggata aggttggcat tggccaggaa aac                                 33

<210> SEQ ID NO 5
<211> LENGTH: 29
<212> TYPE: DNA
<213> ORGANISM: Artificial Sequence
<220> FEATURE:
<223> OTHER INFORMATION: ONYX-053

<400> SEQUENCE: 5
ccaaccttat cctagccggt gtaagcttc                                      29

<210> SEQ ID NO 6
<211> LENGTH: 29
<212> TYPE: DNA
<213> ORGANISM: Artificial Sequence
<220> FEATURE:
<223> OTHER INFORMATION: ONYX-053; H260A MUTATION

<400> SEQUENCE: 6
gaagcttaca ccggctagga taaggttgg                                      29

<210> SEQ ID NO 7
<211> LENGTH: 30

```
<212> TYPE: DNA
<213> ORGANISM: Artificial Sequence
<220> FEATURE:
<223> OTHER INFORMATION: ONYX-054

<400> SEQUENCE: 7
gggtttaaca ataccgccgt ggaagcctgg                              30

<210> SEQ ID NO 8
<211> LENGTH: 30
<212> TYPE: DNA
<213> ORGANISM: Artificial Sequence
<220> FEATURE:
<223> OTHER INFORMATION: ONYX-054; C271A MUTATION

<400> SEQUENCE: 8
ccaggcttcc acggcggtat tgttaaaccc                              30

<210> SEQ ID NO 9
<211> LENGTH: 31
<212> TYPE: DNA
<213> ORGANISM: Artificial Sequence
<220> FEATURE:
<223> OTHER INFORMATION: ONYX-056

<400> SEQUENCE: 9
cgatgtaagg gttgcgggct gtgcctttta c                            31

<210> SEQ ID NO 10
<211> LENGTH: 31
<212> TYPE: DNA
<213> ORGANISM: Artificial Sequence
<220> FEATURE:
<223> OTHER INFORMATION: ONYX-056; R281A MUTATION

<400> SEQUENCE: 10
gtaaaaggca cagcccgcaa cccttacatc g                            31

<210> SEQ ID NO 11
<211> LENGTH: 27
<212> TYPE: DNA
<213> ORGANISM: Artificial Sequence
<220> FEATURE:
<223> OTHER INFORMATION: ONYX-057

<400> SEQUENCE: 11
gtaagggttc gggcctgtgc cttttac                                 27

<210> SEQ ID NO 12
<211> LENGTH: 27
<212> TYPE: DNA
<213> ORGANISM: Artificial Sequence
<220> FEATURE:
<223> OTHER INFORMATION: ONYX-057; G282A MUTATION

<400> SEQUENCE: 12
gtaaaaggca caggcccgaa cccttac                                 27

<210> SEQ ID NO 13
<211> LENGTH: 40
<212> TYPE: DNA
<213> ORGANISM: Artificial Sequence
<220> FEATURE:
<223> OTHER INFORMATION: ONYX-058

<400> SEQUENCE: 13
```

```
gtaagggttc ggggctgttc cttttactgc tgctggaagg                                40
```

<210> SEQ ID NO 14
<211> LENGTH: 40
<212> TYPE: DNA
<213> ORGANISM: Artificial Sequence
<220> FEATURE:
<223> OTHER INFORMATION: ONYX-058; A284A MUTATION

<400> SEQUENCE: 14

```
ccttccagca gcagtaaaag gaacagcccc gaacccttac                                40
```

<210> SEQ ID NO 15
<211> LENGTH: 37
<212> TYPE: DNA
<213> ORGANISM: Artificial Sequence
<220> FEATURE:
<223> OTHER INFORMATION: ONYX-059

<400> SEQUENCE: 15

```
ggttcggggc tgtgccttat actgctgctg gaagggg                                   37
```

<210> SEQ ID NO 16
<211> LENGTH: 37
<212> TYPE: DNA
<213> ORGANISM: Artificial Sequence
<220> FEATURE:
<223> OTHER INFORMATION: ONYX-059; F285L MUTATION

<400> SEQUENCE: 16

```
cccct tccag cagcagtata aggcacagcc ccgaacc                                  37
```

<210> SEQ ID NO 17
<211> LENGTH: 39
<212> TYPE: DNA
<213> ORGANISM: Artificial Sequence
<220> FEATURE:
<223> OTHER INFORMATION: ONYX-060

<400> SEQUENCE: 17

```
gggctgtgcc ttttactgcg cctggaaggg ggtggtgtg                                 39
```

<210> SEQ ID NO 18
<211> LENGTH: 39
<212> TYPE: DNA
<213> ORGANISM: Artificial Sequence
<220> FEATURE:
<223> OTHER INFORMATION: ONYX-060; C288A MUTATION

<400> SEQUENCE: 18

```
cacaccaccc ccttccaggc gcagtaaaag gcacagccc                                 39
```

<210> SEQ ID NO 19
<211> LENGTH: 41
<212> TYPE: DNA
<213> ORGANISM: Artificial Sequence
<220> FEATURE:
<223> OTHER INFORMATION: ONYX-061

<400> SEQUENCE: 19

```
gctgtgcctt ttactgctgc tttaaggggg tggtgtgtcg c                              41
```

<210> SEQ ID NO 20
<211> LENGTH: 41
<212> TYPE: DNA
<213> ORGANISM: Artificial Sequence

```
<220> FEATURE:
<223> OTHER INFORMATION: ONYX-061; W289F MUTATION

<400> SEQUENCE: 20
gcgacacacc accccttaa agcagcagta aaaggcacag c                    41

<210> SEQ ID NO 21
<211> LENGTH: 40
<212> TYPE: DNA
<213> ORGANISM: Artificial Sequence
<220> FEATURE:
<223> OTHER INFORMATION: ONYX-062

<400> SEQUENCE: 21
gctgtgcctt ttactgctgc gcgaaggggg tggtgtgtcg                     40

<210> SEQ ID NO 22
<211> LENGTH: 40
<212> TYPE: DNA
<213> ORGANISM: Artificial Sequence
<220> FEATURE:
<223> OTHER INFORMATION: ONYX-062; W289A MUTATION

<400> SEQUENCE: 22
cgacacacca ccccttcgc gcagcagtaa aaggcacagc                      40

<210> SEQ ID NO 23
<211> LENGTH: 22
<212> TYPE: DNA
<213> ORGANISM: Artificial Sequence
<220> FEATURE:
<223> OTHER INFORMATION: ONYX-063

<400> SEQUENCE: 23
ctgctgctgg gcggggtgg tg                                         22

<210> SEQ ID NO 24
<211> LENGTH: 22
<212> TYPE: DNA
<213> ORGANISM: Artificial Sequence
<220> FEATURE:
<223> OTHER INFORMATION: ONYX-063; K290A MUTATION

<400> SEQUENCE: 24
caccaccccc gcccagcagc ag                                        22

<210> SEQ ID NO 25
<211> LENGTH: 38
<212> TYPE: DNA
<213> ORGANISM: Artificial Sequence
<220> FEATURE:
<223> OTHER INFORMATION: ONYX-064

<400> SEQUENCE: 25
tggaaggggg tggtgtgtgc ccccaaaagc agggcttc                       38

<210> SEQ ID NO 26
<211> LENGTH: 38
<212> TYPE: DNA
<213> ORGANISM: Artificial Sequence
<220> FEATURE:
<223> OTHER INFORMATION: ONYX-064; R295A MUTATION

<400> SEQUENCE: 26
gaagccctgc ttttgggggc acacaccacc cccttcca                       38
```

<210> SEQ ID NO 27
<211> LENGTH: 42
<212> TYPE: DNA
<213> ORGANISM: Artificial Sequence
<220> FEATURE:
<223> OTHER INFORMATION: ONYX-065

<400> SEQUENCE: 27
ggtggtgtgt cgccccgcaa gcagggcttc aattaagaaa tg        42

<210> SEQ ID NO 28
<211> LENGTH: 42
<212> TYPE: DNA
<213> ORGANISM: Artificial Sequence
<220> FEATURE:
<223> OTHER INFORMATION: ONYX-065; K297A MUTATION

<400> SEQUENCE: 28
catttcttaa ttgaagccct gcttgcgggg cgacacacca cc        42

<210> SEQ ID NO 29
<211> LENGTH: 43
<212> TYPE: DNA
<213> ORGANISM: Artificial Sequence
<220> FEATURE:
<223> OTHER INFORMATION: ONYX-066

<400> SEQUENCE: 29
ccaaaagcag ggcttcaatt gcgaaatgcc tctttgaaag gtg        43

<210> SEQ ID NO 30
<211> LENGTH: 43
<212> TYPE: DNA
<213> ORGANISM: Artificial Sequence
<220> FEATURE:
<223> OTHER INFORMATION: ONYX-066; K303A MUTATION

<400> SEQUENCE: 30
cacctttcaa agaggcattt cgcaattgaa gccctgcttt tgg        43

<210> SEQ ID NO 31
<211> LENGTH: 45
<212> TYPE: DNA
<213> ORGANISM: Artificial Sequence
<220> FEATURE:
<223> OTHER INFORMATION: ONYX-067

<400> SEQUENCE: 31
cttcaattaa gaaatgcctc tttgcaaggt gtaccttggg tatcc        45

<210> SEQ ID NO 32
<211> LENGTH: 45
<212> TYPE: DNA
<213> ORGANISM: Artificial Sequence
<220> FEATURE:
<223> OTHER INFORMATION: ONYX-067; E308A MUTATION

<400> SEQUENCE: 32
ggatacccaa ggtacacctt gcaaagaggc atttcttaat tgaag        45

<210> SEQ ID NO 33
<211> LENGTH: 47
<212> TYPE: DNA
<213> ORGANISM: Artificial Sequence
<220> FEATURE:
<223> OTHER INFORMATION: ONYX-068

<400> SEQUENCE: 33
tcaattaaga aatgcctctt tgaagcgtgt accttgggta tcctgtc                47

<210> SEQ ID NO 34
<211> LENGTH: 47
<212> TYPE: DNA
<213> ORGANISM: Artificial Sequence
<220> FEATURE:
<223> OTHER INFORMATION: ONYX-068; R309A MUTATION

<400> SEQUENCE: 34
gacaggatac ccaaggtaca cgcttcaaag aggcatttct taattga                47

<210> SEQ ID NO 35
<211> LENGTH: 39
<212> TYPE: DNA
<213> ORGANISM: Artificial Sequence
<220> FEATURE:
<223> OTHER INFORMATION: ONYX-069

<400> SEQUENCE: 35
taccttgggt atcctgtctg cgggtaactc cagggtgcg                39

<210> SEQ ID NO 36
<211> LENGTH: 39
<212> TYPE: DNA
<213> ORGANISM: Artificial Sequence
<220> FEATURE:
<223> OTHER INFORMATION: ONYX-069; E317A MUTATION

<400> SEQUENCE: 36
cgcaccctgg agttacccgc agacaggata cccaaggta                39

<210> SEQ ID NO 37
<211> LENGTH: 41
<212> TYPE: DNA
<213> ORGANISM: Artificial Sequence
<220> FEATURE:
<223> OTHER INFORMATION: ONYX-070

<400> SEQUENCE: 37
taccttgggt atcctgtctg aggctacctc cagggtccgc c              41

<210> SEQ ID NO 38
<211> LENGTH: 41
<212> TYPE: DNA
<213> ORGANISM: Artificial Sequence
<220> FEATURE:
<223> OTHER INFORMATION: ONYX-070; G318A* MUTATION
<220> FEATURE:
<221> NAME/KEY: misc_feature
<223> OTHER INFORMATION: ONYX-070 had two amino acids changed: Gly 318
      to Ala, and Asn 319 to Thr.

<400> SEQUENCE: 38
ggcggaccct ggaggtagcc tcagacagga tacccaaggt a              41

<210> SEQ ID NO 39
<211> LENGTH: 41
<212> TYPE: DNA
<213> ORGANISM: Artificial Sequence
<220> FEATURE:
<223> OTHER INFORMATION: ONYX-071

<400> SEQUENCE: 39

```
taccttgggt atcctgtctg aggctaactc cagggtgcgc c                          41
```

<210> SEQ ID NO 40
<211> LENGTH: 41
<212> TYPE: DNA
<213> ORGANISM: Artificial Sequence
<220> FEATURE:
<223> OTHER INFORMATION: ONYX-071; G318A-N MUTATION

<400> SEQUENCE: 40

```
ggcgcaccct ggagttagcc tcagacagga tacccaaggt a                          41
```

<210> SEQ ID NO 41
<211> LENGTH: 41
<212> TYPE: DNA
<213> ORGANISM: Artificial Sequence
<220> FEATURE:
<223> OTHER INFORMATION: ONYX-080

<400> SEQUENCE: 41

```
ctaagatatt gcttgagccg gcgagcatgt ccaaggtgaa c                          41
```

<210> SEQ ID NO 42
<211> LENGTH: 41
<212> TYPE: DNA
<213> ORGANISM: Artificial Sequence
<220> FEATURE:
<223> OTHER INFORMATION: ONYX-080; E421A MUTATION

<400> SEQUENCE: 42

```
gttcaccttg gacatgctcg ccgcctcaag caatatctta g                          41
```

<210> SEQ ID NO 43
<211> LENGTH: 37
<212> TYPE: DNA
<213> ORGANISM: Artificial Sequence
<220> FEATURE:
<223> OTHER INFORMATION: ONYX-081

<400> SEQUENCE: 43

```
gagcccgaga gcatgtccgc ggtgaacctg aacgggg                               37
```

<210> SEQ ID NO 44
<211> LENGTH: 37
<212> TYPE: DNA
<213> ORGANISM: Artificial Sequence
<220> FEATURE:
<223> OTHER INFORMATION: ONYX-081; K425 A MUTATION

<400> SEQUENCE: 44

```
ccccgttcag gttcaccgcg gacatgctct cgggctc                               37
```

<210> SEQ ID NO 45
<211> LENGTH: 40
<212> TYPE: DNA
<213> ORGANISM: Artificial Sequence
<220> FEATURE:
<223> OTHER INFORMATION: ONYX-082

<400> SEQUENCE: 45

```
gaacctgaac ggggtgtttg ccatgaccat gaagatctgg                            40
```

<210> SEQ ID NO 46
<211> LENGTH: 40
<212> TYPE: DNA
<213> ORGANISM: Artificial Sequence

```
<220> FEATURE:
<223> OTHER INFORMATION: ONYX-082; D433A MUTATION

<400> SEQUENCE: 46
ccagatcttc atggtcatgg caaacacccc gttcaggttc                              40

<210> SEQ ID NO 47
<211> LENGTH: 29
<212> TYPE: DNA
<213> ORGANISM: Artificial Sequence
<220> FEATURE:
<223> OTHER INFORMATION: ONYX-083

<400> SEQUENCE: 47
ccatgaagat ctgggcggtg ctgaggtac                                          29

<210> SEQ ID NO 48
<211> LENGTH: 29
<212> TYPE: DNA
<213> ORGANISM: Artificial Sequence
<220> FEATURE:
<223> OTHER INFORMATION: ONYX-083; K440A MUTATION

<400> SEQUENCE: 48
gtacctcagc accgcccaga tcttcatgg                                          29

<210> SEQ ID NO 49
<211> LENGTH: 26
<212> TYPE: DNA
<213> ORGANISM: Artificial Sequence
<220> FEATURE:
<223> OTHER INFORMATION: ONYX-084

<400> SEQUENCE: 49
ggaaggtgct ggcgtacgat gagacc                                             26

<210> SEQ ID NO 50
<211> LENGTH: 26
<212> TYPE: DNA
<213> ORGANISM: Artificial Sequence
<220> FEATURE:
<223> OTHER INFORMATION: ONYX-084; R443A MUTATION

<400> SEQUENCE: 50
ggtctcatcg tacgccagca ccttcc                                             26

<210> SEQ ID NO 51
<211> LENGTH: 29
<212> TYPE: DNA
<213> ORGANISM: Artificial Sequence
<220> FEATURE:
<223> OTHER INFORMATION: ONYX-085

<400> SEQUENCE: 51
ggaaggtgct gagggccgat gagacccgc                                          29

<210> SEQ ID NO 52
<211> LENGTH: 29
<212> TYPE: DNA
<213> ORGANISM: Artificial Sequence
<220> FEATURE:
<223> OTHER INFORMATION: ONYX-085; Y444A MUTATION

<400> SEQUENCE: 52
gcgggtctca tcggccctca gcaccttcc                                          29
```

ADENOVIRUS E1B-55K SINGLE AMINO ACID MUTANTS AND METHODS OF USE

CROSS-REFERENCE TO RELATED APPLICATIONS

This application is a divisional of U.S. patent application Ser. No. 09/918,696, filed Jul. 30, 2001, now U.S. Pat. No. 6,635,244, which claims the benefit of U.S. Provisional Application Ser. No. 60/222,887, filed Aug. 3, 2000.

TECHNICAL FIELD

The invention is in the field of cancer therapy and provides compositions of recombinant cytopathic adenoviruses that express mutant E1B-55K protein, and methods of using such adenoviruses for treating neoplastic disease.

BACKGROUND

From the early part of this century, viruses have been used to treat cancer. The approach has been two-fold; first, to isolate or generate oncolytic viruses that selectively replicate in and kill neoplastic cells, while sparing normal cells. Investigators initially used wild type viruses, and this approach met with some, albeit, limited success. While oncolysis and slowing of tumor growth occurred with little or no damage to normal tissue, there was no significant alteration in the course of the disease. See, Smith et al., Cancer 9: 1211-1218 (1956), Cassel, W. A. et al., Cancer 18: 863-868 (1965), Webb, H. E. et al., Lancet 1: 1206-1209 (1966). See, also, Kenney, S and Pagano, J. J. Natl. Cancer Inst., vol. 86, no. 16, p.1185 (1994).

More recently, and because of the reoccurrence of disease associated with the limited efficacy of the use of wild type viruses, investigators have resorted to using recombinant viruses that can be delivered at high doses, and that are replication competent in neoplastic but not normal cells. Such viruses are effective oncolytic agents in their own right, and further, can be engineered to carry and express a transgene that enhances the anti neoplastic activity of the virus. An example of this class of viruses is an adenovirus that is mutant in the E1B region of the viral genome. See, U.S. Pat. No. 5,677,178, and Bischoff, J. R., D. H. Kim, A. Williams, C. Heise, S. Horn, M. Muna, L. Ng, J. A. Nye, A. Sampson-Johannes, A. Fattaey, and F. McCormick. 1996, Science. 274: 373-6.

The approach described in U.S. Pat. No. 5,677,178, inventor, McCormick takes advantage of the loss of tumor suppressor proteins in cancer cells, particularly p53. A function of p53 is to inhibit the progression of mammalian cells through the cell cycle in response to DNA damage. The E1b-55K protein of wild-type adenovirus binds to p53 in adenovirus infected cells that exhibit p53 and produce a substantial inactivation of p53 function. Functional adenoviral E1b-55K protein is essential for efficient adenoviral replication in cells containing functional p53. Adenovirus mutants which substantially lack the ability to bind p53 are replication deficient in non-replicating, non-neoplastic cells having normal levels of functional p53. However, such adenoviral mutants exhibit a replication phenotype in cells which are deficient in p53 function (for example, cells which are homozygous for substantially deleted p53 alleles, cells which comprise mutant p53 proteins which are essentially non-functional) and thus cause the death of such cells.

There are several reports on adenoviral mutants which substantially lack the ability to bind p53 resulting from a mutation in the E1B-55K protein. Such viruses generally have some, or all of the E1B-55K region deleted.

U.S. Pat. No. 5,677,178, inventor, McCormick, describes, among other things, adenoviral mutants that lack a viral oncoprotein, that is E1B-55K protein or E4 orf6, capable of binding p53.

U.S. Pat. No. 6,080,578 describes, among other things, adenoviral mutants that have deletions in the region of the E1b-55K protein that is responsible for binding p53.

There are several publications which suggest that in certain tumor cells which have p53 that the presence of p53 may not be predictive of the efficacy of an adenovirus that encodes an E1b-55K protein that is defective in binding p53. See, for example, Goodrum and Ornelles J. Virol. 1998, Vol. 72: 9479-9490; Hall, et al., 1998, Nat. Med. 4: 1068-1072; Hay, et al., 1999, Hum., Gene Ther. 10: 579-590; Rothmann, et al., 1998, J. Virol. 72: 9470-9478; and Turnell, et al., 1999, J. Virol. 73: 2074-2083. It is believed that in these cells that there is a defect in the p53 pathway, and thus such cells lack functional p53, and consequently also support replication of adenoviral mutants that encode an E1b-55K protein that is defective in binding p53.

The adenoviral E1B-55K protein plays an important role during the productive infection of human adenovirus type 5 (Ad5). In the early phase of infection, E1B-55K forms a stable complex with p53 (Sarnow, P., et al., Virology, 1982, vol. 120: p. 510-517), and inhibits p53-mediated transcriptional activation (Yew, P. R. and A. J. Berk, Nature, 1992, vol. 357: p. 82-85; and Yew, P. R., et al., Genes Dev., 1994, vol. 8: 1994). Furthermore, E1B-55K and another adenoviral protein, E4orf6, co-operate to relocate p53 to the cytoplasm for active degradation (Querido, E., et al., J. Virol. 1997, vol. 71: p. 3788-3798; Roth, J. et al., J. Virol. 1998; vol. 72: p. 8510-8516; and Steegenga, W. T., et al., Oncogene, 1998, vol. 16: p. 349-357). This inactivation of p53 is critical for the replication of adenovirus, which requires cells to enter S phase. During the late phase of infection with Ad5, viral mRNAs are selectively exported to the cytoplasm and are efficiently translated, while the nucleocytoplasmic transport of most host cell mRNAs is inhibited (Beltz, G. A. and S. J. Flint, J. Mol. Biol., 1979, vol. 131: p. 353-373; Babiss, L., et al., Mol. Cell. Biol., 1985, vol. 5: p. 2552-2558; Pilder, S., et al., Mol. Cell. Biol., 1986: vol. 6: p. 470-476). This selective accumulation of viral mRNAs during the late phase of infection is mediated by a protein complex that includes E1B-55K and E4orf6 (Sarnow, P., et al., J. Virol., 1984, vol. 49: p. 692-700; and Halbert, et al., J. Virol., 1985, vol. 56: p. 250-257; and, Bridge, E. and G. Ketner, Virology, 1990, vol. 174: p. 345-353) This complex actively shuttles between the nucleus and the cytoplasm, serving as a nucleocytoplasmic transporter for viral mRNAs (Dobbelstein, M. et al., EMBO J., 1997, vol. 16: p. 4267-4284).

In clinical trials that are still ongoing, an adenovirus mutant, ONYX-015, that lacks the ability to bind p53 has been shown to be biologically active and cause partial tumor necrosis in head and neck cancer. ONYX-015, originally named dl 1520, is a mutant adenovirus that does not express the E1B-55K protein (Barker, D. D. and A. J. Berk, Virology, 1987, vol: 156: p. 107-121). This virus contains a stop codon immediately following the translation initiation codon ATG, plus a large deletion of the E1B-55K coding sequence. These mutations result in the complete abrogation of E1B-55K expression but do not alter the expression of the E1B-19K protein encoded in an overlapping open reading frame. Consequently, this virus lacks the ability to bind and inactivate p53, allowing it to replicate substantially selectively in tumor cells that are defective in p53 function but not in normal cells where p53 function is normal (Bischoff, J. R., et al., Science, 1996, vol. 274: p. 373-376; and, Heise, C., et al., Nat. Med., 1997, vol. 3: p. 639-645). This forms the foundation of utilizing ONYX-015 as an anti-tumor agent.

While the lack of E1B-55K function in ONYX-015 permits viral replication in tumor cells that lack p53 function, the virus is also defective in cytoplasmic accumulation of the viral late mRNAs, host cell shut-off, and translation of late mRNAs. Thus, the mutation in ONYX-015 compromises the ability of the mutant virus to reproduce itself in tumor cells. As such, it would be highly desirable to create an E1B-55K mutant that fails to bind and inactivate p53, yet is still capable of performing the late viral functions. Such a mutation would allow the virus to replicate selectively in cells that are deficient in p53 function without compromising the efficiency of the virus to replicate in tumor cells. The present invention fulfills these and other needs.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

The present invention provides a novel class of E1B-55K adenoviral mutants and methods of making and using the same to ablate neoplastic cells.

Another aspect of the invention described herein is a description of E1B-55K adenoviral mutants which are substantially incapable of binding the tumor suppressor, p53, yet retain certain of the viral functions associated with wild type adenovirus.

A further aspect of the invention is the description of E1B-55K adenoviral point mutants that are mutated in the region of E1B-55K that binds the tumor suppressor p53 thus rendering such mutated protein substantially incapable of binding p53, yet retain certain of the replicative functions associated with wild type adenovirus.

Another aspect of the invention is a method for selectively and substantially ablating neoplastic cells in a cell population consisting of normal and neoplastic cells with an E1B55K adenoviral point mutants that are mutated in the region of 55K. Such mutants either lack a single amino acid that binds the tumor suppressor p53, or such amino acid is substituted with another amino acid that does not bind p53. Regardless, such mutants retain certain of the replicative functions associated with wild type adenovirus A further object of the invention is the description of a method for treating neoplasia consisting of administering to a patient in need of such treatment an E1B-55K adenoviral point mutant that is mutated in the region of 55K that binds the tumor suppressor p53, yet retain certain of the replicative functions associated with wild type adenovirus in combination with chemotherapy.

These and other objects of the present invention will become apparent to one of ordinary skill in the art upon reading the description of the various aspects of the invention in the following specification. The foregoing and other aspects of the present invention are explained in greater detail in the drawings, detailed description, and examples set forth below.

Accordingly, in one aspect, the present invention relates to a recombinant adenovirus comprising a mutation in the E1B-55K gene that encodes a mutated E1B-55K protein comprising a single amino acid mutation, the mutation substantially reducing the ability of the E1B-55K mutated protein to bind to the tumor suppressor p53. Examples of such recombinant adenoviruses include Onyx 051 and Onyx 053. The recombinant adenoviruses of may further comprise the property of substantially retaining late functions of the virus.

In a second aspect, the present invention relates to an isolated adenoviral E1B-55K protein comprising a single amino acid mutation wherein the mutation is selected from the group consisting of amino acids at positions 240 or 260 of the protein.

In a third aspect, the present invention relates to an isolated polynucleotide wherein the polynucleotide comprises mutated adenoviral DNA that encodes a E1B-55K protein, the protein comprising a single amino acid mutation which mutation substantially reduces the capacity of the protein to bind to the tumor suppressor, p53. In one embodiment of the invention, the isolated polynucleotide is RNA.

In a fourth aspect, the present invention relates to a method of treating cancer in a patient in need of the treatment, comprising administering to the patient a dose of a recombinant adenovirus, the adenovirus comprising a mutation in the E1B-55K gene that encodes a mutated E1B-55K protein comprising a single amino acid mutation, the mutation substantially reducing the ability of the E1B-55K mutated protein to bind to the tumor suppressor p53, and allowing sufficient time for the adenovirus to infect the cancer, and repeating the treatment if desired. In one embodiment, the method may further comprise administering the recombinant adenovirus with a chemotherapeutic. Examples of the recombinant adenoviruses are Onyx 051 or Onyx 053.

In a fifth aspect, the present invention relates to a method of treating cancer in a patient in need of the treatment, comprising administering to the patient a dose of an isolated polynucleotide wherein the polynucleotide comprises mutated adenoviral DNA that encodes an E1B-55K protein, the protein comprising a single amino acid mutation which mutation substantially reduces the capacity of the protein to bind to the tumor suppressor, p53, and repeating the treatment if desired. In one embodiment, the isolated polynucleotide is RNA. In another embodiment, the isolated polynucleotide encodes the E1B-55K protein and the protein comprises a mutation at position 240 or position 260 of the protein. In yet another embodiment, the method may further comprise administering the polynucleotide with a chemotherapeutic. In one embodiment of the method, the polynucleotide is administered with a liposome.

BRIEF DESCRIPTION OF THE DRAWING

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
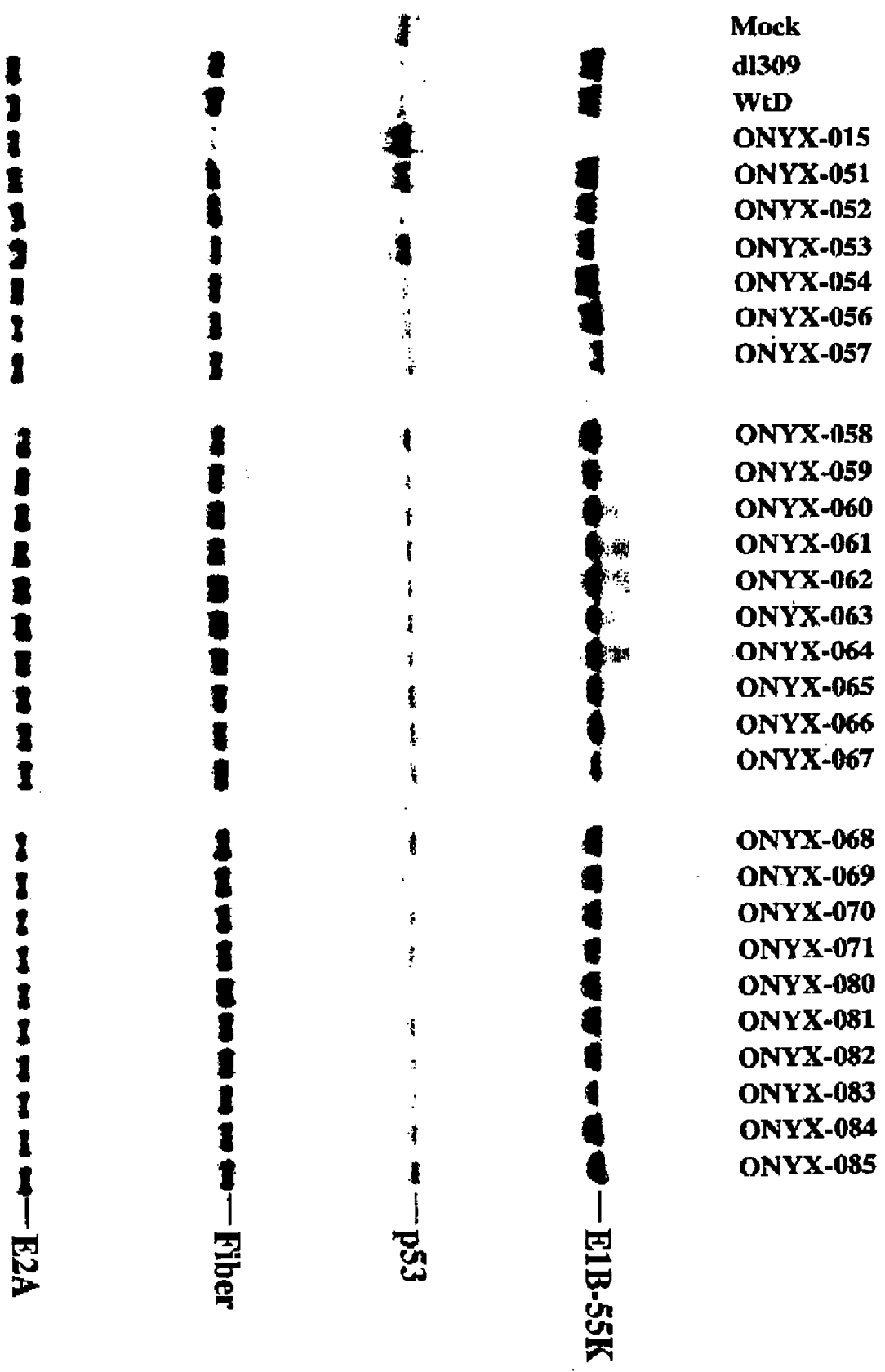
FIG. 1. Effects of E1B-55K mutations on p53 accumulation and viral gene expression. A549 cells were either mock infected or infected with dl309, WtD, ONYX-015 or viruses expressing various E1B-55K mutants. All infections were performed at MOI of 10. Cell extracts were prepared at 24 hours post infection (hpi) and separated by SDS-PAGE. Steady-state levels of E1B-55K mutants, p53, E2A and fiber were determined by Western blotting with monoclonal antibodies 2A6, DO-1, B6-6, and a polyclonal antibody against fiber, respectively. Blots were visualized with ECL, as described in the Examples.

All publications and patent applications mentioned in this specification are herein incorporated by reference to the same extent as if each individual publication or patent application was specifically and individually indicated to be incorporated by reference.

Definitions

Unless defined otherwise, all technical and scientific terms used herein have the same meaning as commonly understood by one of ordinary skill in the art to which this invention belongs. Generally, the nomenclature used herein and the laboratory procedures described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (see generally, Sambrook et al., *Molecular Cloning: A Laboratory Manual*, 2nd. edition (1989) Cold Spring Harbor Laboratory Press, Cold Spring Harbor, N.Y., which is incorporated herein by reference) which are provided throughout this document. The nomenclature used herein and the laboratory procedures in analytical chemistry, organic synthetic chemistry, and pharmaceutical formulation described below are those well known and commonly employed in the art. Standard techniques are used for chemical syntheses, chemical analyses, pharmaceutical formulation and delivery, and treatment of patients.

As employed throughout the disclosure, the following terms, unless otherwise indicated, shall be understood to have the following meanings:

The term "adenovirus" indicates over 40 adenoviral subtypes isolated from humans, and as many from other mammals and birds. See, Strauss, "Adenovirus infections in humans," in *The Adenoviruses*, Ginsberg, ed., Plenum Press, New York, N.Y., pp. 451-596 (1984). The term preferably applies to two human serotypes, Ad2 and Ad5.

By "mutation" or "mutant" in the context as referred to herein relating to the adenoviral E1B-55K protein means a deletion or substitution of single amino acids which deletion or substitution causes a substantial loss in the binding activity of E1B-55K to the tumor suppressor, p53.

The terms "early" and "late" as referred to the expression of Ad genes means those genes expressed during the early and late phase of the virus life cycle. Early genes are those transcribed prior to replication of the genome while late genes are transcribed after replication. The early genes comprise E1a, E1b, E2a, E2b, E3 and E4. The E1a gene products are involved in transcriptional regulation; the E1b gene products are involved in the shut-off of host cell functions and mRNA transport. E2a encodes the a DNA-binding protein (DBP); E2b encodes the viral DNA polymerase and preterminal protein (pTP). The E3 gene products are not essential for viral growth in cell culture. The E4 region encodes regulatory proteins involved in transcriptional and post-transcriptional regulation of viral gene expression; a subset of the E4 proteins are essential for viral growth. The products of the late genes (e.g., L1-5) are predominantly components of the virion as well as proteins involved in the assembly of virions.

"Neoplastic cells" or "neoplasia" refer to cells which exhibit relatively autonomous growth, so that they exhibit an aberrant growth phenotype characterized by a significant loss of control of cell proliferation. Neoplastic cells comprise cells which may be actively replicating or in a temporary non-replicative resting state ($G_1$ or $G_0$); similarly, neoplastic cells may comprise cells which have a well-differentiated phenotype, a poorly-differentiated phenotype, or a mixture of both type of cells. Thus, not all neoplastic cells are necessarily replicating cells at a given timepoint. The set defined as neoplastic cells consists of cells in benign neoplasms and cells in malignant (or frank) neoplasms. Herein frankly neoplastic cells are frequently referred to as cancer, or cancer cells, typically termed carcinoma if originating from cells of endodermal or ectodermal histological origin, or sarcoma if originating from cell types derived from mesoderm. Included within the definition of neoplastic cells are cells that lack p53 function, but are not frankly neoplastic. See. U.S. Pat. No. 5,677,178. Examples of cells in the later category would be cells associated with Barrett's syndome, or leukoplakia.

"Physiological conditions," or "physiological solution" refers to an aqueous environment having an ionic strength, pH, and temperature substantially similar to conditions in an intact mammalian cell or in a tissue space or organ of a living mammal. Typically, physiological conditions comprise an aqueous solution having about 150 mM NaCl, pH 6.5-7.6, and a temperature of approximately 22-37° C. Generally, physiological conditions are suitable binding conditions for intermolecular association of biological macromolecules. For example, physiological conditions of 150 mM NaCl, pH 7.4, at 37° C. are generally suitable.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes (e.g., $^3H$, $^{14}C$, $^{35}S$, $^{125}I$, $^{131}I$), fluorescent labels (e.g., FITC, rhodamine, lanthanide phosphors), enzymatic labels (e.g., horseradish peroxidase, b-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

Chemistry terms herein are used according to conventional usage in the art, as exemplified by The McGraw-Hill Dictionary of Chemical Terms (ed. Parker, S., 1985), McGraw-Hill, San Francisco, incorporated herein by reference.

In the formulae representing selected specific embodiments of the present invention, the amino- and carboxy-terminal groups, although often not specifically shown, will be understood to be in the form they would assume at physiological pH values, unless otherwise specified. Thus, the N-terminal $H_2^+$ and C-terminal-$O^-$ at physiological pH are understood to be present though not necessarily specified and shown, either in specific examples or in generic formulas. In the polypeptide notation used herein, the left hand end of the molecule is the amino terminal end and the right hand end is the carboxy-terminal end, in accordance with standard usage and convention. Of course, the basic and acid addition salts including those which are formed at non-physiological ph values are also included in the compounds of the invention. The amino acid residues described herein are preferably in the "L" isomeric form. Stereoisomers (e.g., D-amino acids) of the twenty conventional amino acids, unnatural amino acids such as a,a-distributed amino acids, N-alkyl amino acids, lactic acid, and other unconventional amino acids may also be suitable components for polypeptides of the present invention, as long as the desired functional property is retained by the polypeptide. For the peptides shown, each encoded residue where appropriate is represented by a three letter designation, corresponding to the trivial name of the conventional amino acid, in keeping with standard polypeptide nomenclature (described in *J. Biol. Chem.*, 243:3552-59 (1969) and adopted at 37 CFR §1.822(b)(2)). Free functional groups, including those at the carboxy- or amino-terminus, referred to as noninterfering substituents, can also be modified by amidation, acylation or other substitution, which can, for example, change the solubility of the compounds without affecting their activity.

The term "polynucleotide" as referred to herein means a polymeric form of nucleotides of at least 10 bases in length, either ribonucleotides (RNA) or deoxynucleotides (DNA) or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset with 200 bases or fewer in length. Preferably oligonucleotides are 10 to 60 bases in length. Oligonucleotides are usually single stranded, e.g. for probes; although oligonucleotides may be double stranded, e.g for use in the construction of a gene mutant. Oligonucleotides of the invention can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like known in the art.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading frame.

All nucleotide sequences follow standard notation, and are in the 5' to 3' orientation.

The term "functionally equivalent codon" refers to codons that encode the same amino acid, and further refers to codons that encode biologically equivalent amino acids Table 1 shows such codons, as well as the single and triple letter abbreviations for the 20 common amino acids.

TABLE 1

Functionally Equivalent Codons.

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | K | AAA AAG |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

For a general description of adenovirus biology, which may be referred to for guidance see, *Virology*, Second edition, eds., Fields B N and Knipe D M, Vol.2, pp. 1651-1740, Raven Press, New York, N.Y., incorporated herein by reference. The following specific descriptions refer to, but are not limited to, adenovirus serotype 5 and adenovirus serotype 2. Although it is believed that other adenoviral serotypes may be used, adenovirus type 5 provides a common reference point for the nucleotide numbering convention of viral polynucleotides and amino acid numbering of viral-encoded polypeptides of the E1a viral gene region, and other viral genes. Adenovirus type 2 provides a convenient reference for the numbering convention of the E1b viral gene region, and other viral gene regions. It is believed that those of skill in the art will readily identify the corresponding positions in other adenoviral serotypes.

A function of the cellular phosphoprotein p53 is to inhibit the progression of mammalian cells through the cell cycle. Wild-type adenovirus E1b p55 protein binds to p53 in infected cells that have p53 and produce a substantial inactivation of p53 function, likely by sequestering p53 in an inactive form. Functional E1b p55 protein is essential for efficient adenoviral replication in cells containing functional p53. Hence, adenovirus variants which substantially lack the ability to bind p53 are replication deficient in non-replicating, non-neoplastic cells having normal levels of functional p53.

Human tumor cells frequently are homozygous or heterozygous for mutated (e.g., substitution, deletion, frameshift mutants) p53 alleles, and lack p53 function necessary for normal control of the cell cycle (Hollstein et al. (1991) Science 253: 49; Levine et al. (1991) op.cit., incorporated herein by reference). Thus, many neoplastic cells are p53$^{(-)}$, either because they lack sufficient levels of p53 protein and/or because they express mutant forms of p53 which are incapable of substantial p53 function, and which may substantially diminish p53 function even when wild-type p53 may be present (e.g., by inhibiting formation of functional multimers). Some neoplastic cells may comprise alleles encoding essentially wild-type p53 proteins, but may comprise a second site mutation that substantially abrogates p53 function, such as a mutation that results in p53 protein being localized in the cytoplasm rather than in the nucleus; such second site mutants also substantially lack p53 function.

It is believed that replication deficient adenovirus species which lack the capacity to complex p53 but substantially retain other essential viral replicative functions will exhibit a replication phenotype in cells which are deficient in p53 function (e.g., cells which are homozygous for substantially deleted p53 alleles, cells which comprise mutant p53 proteins which are essentially nonfunctional) but will not substantially exhibit a replicative phenotype in non-replicating, non-neoplastic cells. Such replication deficient adenovirus species are referred to herein for convenience as E1b-p53$^{(-)}$ replication deficient adenoviruses.

A particular class of E1b-p53$^{(-)}$ replication deficient adenoviruses contains a stop codon immediately following the translation initiation codon ATG, plus a large deletion of the E1B-55K coding sequence. These mutations result in the complete abrogation of E1B-55K expression, and an example of this type of virus is ONYX-015, originally named dl1520 (Barker, DD, 1988).

This type of vector is defective in cytoplasmic accumulation of the viral late mRNAs, host cell shut-off, and translation of late mRNAs, thus compromising the ability of the mutant virus to reproduce itself to high levels. Thus, it is desirable to create an E1B-55K mutant that fails to bind and inactivate p53, yet is still capable of performing the late functions. Such a mutation would allow the virus to replicate robustly and selectively in cells that are deficient in p53 function without compromising the efficiency of the virus to replicate in tumor cells.

A basis of the present invention is that the regions of the E1B-55K protein that mediate these functions appear to overlap with one another. The region of E1B-55K that mediates its interaction with p53 has been mapped to amino acid 224 to 354 (Kao, C C. et al., Virology, 1990, vol. 179: p. 806-814; and, Yew, P. R., et al., Virology, 1990, vol. 179: p. 795-805). The same region appears to be critical for E1B-55K's ability to mediate mRNA transport. The regions required for E4orf6 binding (Rubenwolf, S., et al., J. Virol., 1997, vol. 71: p. 1115-1123), the regions required to bind E1B-AP5, a cellular protein implicated in nucleocytoplasmic transport (Gabler, S., et al., J. Virol., 1998, vol. 72: p. 7960-7971), and the regions of E1B-55K that have RNA binding capability (Horridge, J. J. and K. N. Leppard, J. Virol., 1998, vol. 72: p. 9374-9379) all partially overlap with the region required for p53 binding. Thus far, all efforts to separate the p53 binding/inactivation and the late functions of the protein have been unsuccessful.

To separate the p53 binding/inactivation function and the late functions of the E1B-55K protein, we have generated single amino acid mutations in the E1B-55K protein in the region of E1B-55K that mediates its interaction with p53, or amino acids 224 to 354 and other regions. (Kao, C C. et al., Virology, 1990, vol. 179: p. 806-814; and, Yew, P. R., et al., Virology, 1990, vol. 179: p. 795-805). These mutations were then characterized relative to ONYX 015 or wild type adenovirus for their ability to modulate p53 level/activity, interact with the E4orf6 protein, mediate viral late gene expression, and support viral replication in human cancer cells.

Construction of Adenovirus E1B-55K Mutants

Methods for the construction of adenoviral mutants are generally known in the art. See, Mittal, S. K., Virus Res., 1993, vol: 28, pages 67-90; and Hermiston, T. et al., Methods in Molecular Medicine: Adenovirus Methods and Protocols, W. S. M. Wold, ed, Humana Press, 1999. Further, the adenovirus 5 genome is registered as Genbank accession #M73260, and the virus is available from the American Type Culture Collection, Rockville, Md., U.S.A., under accession number VR-5.

Generally, adenovirus vector construction involves an initial deletion or modification of a desired region of the adenoviral genome, preferably the Ad5 genome, in a plasmid cassette using standard techniques.

Certain of the materials and methods used to construct adenovirus mutants are described by Hanke, T., et. al. (1990) Virology, vol. 177, pages 437-444, and Bett, A. J., et. al., (993) J. Virol. vol. 67, pages 5911-5921, and in PCT/CA96/00375. Microbix Biosystems, Inc., located at 341 Bering Avenue, Toronto, Ontario Canada, sells many of the materials used to construct adenovirus mutants, and provides Product Information Sheets on how to make them. See also, Hermiston, T. et al., Methods in Molecular Medicine: Adenovirus Methods and Protocols, W. S. Wold, ed, Humana Press, 1999.

Tumor cell lines that were used to conduct the experiments described herein are readily available. For example A549, 293, U2OS, DU 145, H 1299 cells were obtained from ATCC. HCT116−/−, a derivative of HCT116 with p53 gene knockout is a generous gift from Dr. F. McCormick, UCSF. Cells are grown under standard growth conditions, preferably as mono-layer cultures in Dulbecco's modified Eagle's medium (DMEM) supplemented with 10% fetal bovine serum (FBS), 100 µg/ml non-essential amino acids, 10 U/ml penicillin and 10 µg/ml streptomycin. All adenovirus infections were performed in DMEM-high glucose supplemented with 2% FBS, 2 mM L-glutamine, 100 μg/ml non-essential amino acids, 10 U/ml penicillin and 10 μg/ml streptomycin.

The preferred procedure for constructing the adenoviral E1b-55K mutants of the instant invention is to make site specific mutations in the adenoviral genome in a plasmid cassette using well established techniques of molecular biology, or modifications of these techniques, referred to herein. This can be realized using various materials and methods.

It is noteworthy that while the instant invention is described in terms of adenovirus type 5, it may be practiced with other similar adenovirus serotypes. The general organization of the adenoviral genome is conserved among serotypes, and specific functions are similarly situated.

More specifically, we have constructed twenty-six single amino acid substitution mutations in the p53-binding domain and the transcriptional repression domain of the E1B-55K protein. These mutations were recombined into an infectious virus, dl309, (see, Jones, N and T. Shenk, Cell, 1979, vol.17: p. 683-689) background and characterized for their abilities to modulate p53 level and activity, interact with the E4orf6 protein, mediate viral late gene expression and host cell shut-off, rescue the cold sensitive phenotype, and support virus replication in human cancer cells. Two E1B-55K mutants, R240A and H260A, appeared to have lost the ability to inactivate p53 but have retained, at least partially, the late functions of the wild-type protein. R240A fully restored the wild-type replication capacity of ONYX-015 in human cancer cells, while H260A did so partially. The ability to separate the p53-inactivation activity and the late functions of E1 B-55K raises the possibility of creating adenovirus variants that replicate more efficiently than ONYX-015 but retain the tumor selectivity of ONYX-015.

It is important to note that while an embodiment of the instant invention are E1B-55K mutants that have alanine substituted for arginine and histidine at positions 240 and 260, respectively, another embodiment is an E1B-55K protein that lacks arginine and histidine at these positions.

While alanine is the preferred amino acid to substitute for arginine and histidine, other amino acids that have similar hydropathic indices may also be employed. See, for example, Kyte, J. and Doolittle, R., J. Mol. Biol., vol. 157:pages 105-132 (1982). Amino acid substitutions for arginine and histidine in the invention E1B-55K protein would be selected based on the relative similarity of the amino acid side-chain substituents, for example, their hydrophobicity, hydrophilicity, charge, size, and the like. An analysis of the size, shape and type of the amino acid side-chain substituents reveals that alanine, glycine and serine are all a similar size; and are defined herein as biologically functional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in establishing similar biological function on a protein is understood in the art (See, Kyte, J. and Doolittle, R., J. Mol. Biol., vol. 157:pages 105-132, 1982). It is known that certain amino acids may be substituted for other amino acids having a similar hydropathic index or score and still retain a similar biological activity. In making changes based upon the hydropathic index, the substitution of amino acids whose hydropathic indices are within ±0.2 is preferred, those which are within ±0.1 are particularly preferred, and those within ±0.05 are even more preferred.

It is also understood in the art that the substitution of like amino acids can be made effectively on the basis of hydrophilicity. U.S. Pat. No. 4,554,101, shows that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±0.1); glutamate (+3.0±0.1); serine (+0.3); asparagine (+0.2); glutamine (+0.2); glycine (0); threonine (−0.4); proline (−0.5±0.1); alanine (−0.5); histidine (−0.5); cysteine (−1.0); methionine (−1.3); valine (−1.5);

leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±0.2 is preferred, those which are within ±0.1 are particularly preferred, and those within ±0.5 are even more particularly preferred.

Another aspect of the instant invention is the incorporation of heterologous genes into the adenoviral genome in a manner so as not to interfer with the expression of the mutant E1B-55K proteins. Thus, such viruses would contain heterologous genes in the preferred E3 region, and optionally in E1A or E4orf6. Examples of such heterologous genes, or fragments thereof that encode biologically active peptides, include those that encode immunomodulatory proteins, and prodrug activators (i.e. cytosine deaminase, thymidine kinase, U.S. Pat. Nos. 5,358,866, and 5,677,178). Examples of the former would include interleukin 2, U.S. Pat. No. 4,738,927 or 5,641,665; interleukin 7, U.S. Pat. No. 4,965,195 or 5,328,988; and interleukin 12, U.S. Pat. No. 5,457,038; tumor necrosis factor alpha, U.S. Pat. No. 4,677,063 or 5,773,582; interferon gamma, U.S. Pat. No. 4,727,138 or 4,762,791; or GM-CSF, U.S. Pat. No. 5,393,870 or 5,391,485. Additional immunomodulatory proteins further include macrophage inflammatory proteins, including MIP-3, (See, Well, T. N. and Peitsch, M C. J. Leukoc. Biol vol. 61 (5): pages 545-50,1997), and cell suicide, or apoptosis inducing proteins, including BAD and BAX. See, Yang, E., et al. Cell, vol. 80, pages 285-291 (1995); and Sandeep, R., et al Cell, vol. 91, pages 231-241 (1997). Monocyte chemotactic protein (MCP-3 alpha) may also be used. A preferred embodiment of a heterologous gene is a chimeric gene consisting of a gene that encodes a protein that traverses cell membranes, for example, VP22 or TAT, fused to a gene that encodes a protein that is preferably toxic to cancer but not normal cells.

The adenoviral E1B-55K mutants of the instant invention can also incorporate a tissue (U.S. Pat. No. 5,998,205) or cell cycle specific promoter, including an E2F responsive promoter (PCT/US97/17143) that will drive the replication of the mutants by controlling a viral gene critical for replication, or the expression of another gene, preferably a negative selection gene. An example of a tissue specific promoter includes prostate specific antigen promoter. See, PCT/US95/14461, or U.S. Pat. No. 5,698,443. Examples of certain negative selection genes include cytosine deaminase, and thymidine kinase. Regarding cytosine deaminase, see, U.S. Pat. Nos. 5,358,866, and 5,677,178.

For example, a HSV tk gene cassette may be operably linked downstream of an E3 promoter in one of the invention adenoviral E1b55K mutants. Frequently, it is desirable to delete a nonessential portion (i.e., for viral replication and packaging) of the adenoviral genome to accommodate the negative selection cassette; thus a substantial portion of the E3 gene region may be deleted and replaced with a negative selection cassette such as an HSV tk gene operably linked to either an E3 promoter, or a tissue specific promoter (and enhancer) or other suitable promoter/enhancer. Alternatively, a negative selection gene may be operably linked to an adenovirus late region promoter to afford efficient expression of the negative selection gene product in cells expressing a replication phenotype characterized by transcription from late gene promoters.

Expression of the HSV tk gene in a cell is not directly toxic to the cell unless the cell is exposed to a negative selection agent such as gancyclovir or FIAU. Infected cells expressing a replication phenotype wherein a negative selection gene is substantially expressed may produce essentially no additional cytotoxicity until the negative selection agent (e.g., gancyclovir) is administered in an effective selective dosage, at which time the infected cells expressing the tk gene and the surrounding tumor cells will be selectively ablated; thus negative selection can be used for enhanced cytopathic killing and/or to damp out further viral replication by killing cells exhibiting a replicative phenotype.

A preferred embodiment is an HSV tk gene cassette (Zjilstra et al. (1989) *Nature* 342:435; Mansour et al. (1988) *Nature* 336: 348; Johnson et al. (1989) *Science* 245: 1234: Adair et al. (1989) *Proc. Natl. Acad. Sci (U.S.A.)* 86: 4574; Capecchi, M. (1989) *Science* 244:1288, incorporated herein by reference) operably linked to an appropriate promoter and/or enhancer with a polyadenylation site to form a tk expression cassette. The tk expression cassette (or other negative selection expression cassette) is inserted into the adenoviral genome, for example, as a replacement for a substantial deletion of the E3 region.

Therapeutic Methods

Therapy of disease, preferably neoplastic disease, wherein the disease arises from a loss of p53 or a defect in the p53 pathway, may be afforded by administering to a patient a composition comprising adenoviral E11355K mutants of the invention, and further comprising a negative selection gene. Examples of the latter would include cytosine deaminase and thymidine kinase.

Various human neoplasms may be treated with the invention adenoviral constructs, particularly in those instances when another region of the viral genome, preferably the E3 region, encodes a protein useful for gene therapy of disease. An example would be a cytokine, preferably an interleukin. For example, but not by way of limitation, a human patient or nonhuman mammal having a bronchogenic carcinoma, nasopharyngeal carcinoma, laryngeal carcinoma, small cell and non-small cell lung carcinoma, lung adenocarcinoma, hepatocarcinoma, pancreatic carcinoma, bladder carcinoma, colon carcinoma, breast carcinoma, cervical carcinoma, ovarian carcinoma, or lymphocytic leukemias may be treated by administering an effective antineoplastic dosage of an appropriate adenovirus. Suspensions of infectious adenovirus particles may be applied to neoplastic tissue by various routes, including intravenous, intraperitoneal, intramuscular, subdermal, and topical. An adenovirus suspension containing about $10^3$ to $10^{14}$ or more virion particles per ml may be inhaled as a mist (e.g., for pulmonary delivery to treat bronchogenic carcinoma, small-cell lung carcinoma, non-small cell lung carcinoma, lung adenocarcinoma, or laryngeal cancer) or swabbed directly on a tumor site for treating a tumor (e.g., bronchogenic carcinoma, nasopharyngeal carcinoma, laryngeal carcinoma, cervical carcinoma) or may be administered by infusion (e.g., into the peritoneal cavity for treating ovarian cancer, into the portal vein for treating hepatocarcinoma or liver metastases from other non-hepatic primary tumors) or other suitable route, including direct injection into a tumor mass (e.g., a breast tumor), enema (e.g., colon cancer), or catheter (e.g., bladder cancer).

The invention adenovirus mutants may be further evaluated by their capacity to reduce tumorigenesis or neoplastic cell burden in nu/nu mice harboring a transplant of neoplastic cells, as compared to untreated mice harboring an equivalent transplant of the neoplastic cells.

Adenoviral therapy using the instant invention E1B 55K mutant viruses may be combined with other antineoplastic protocols, such as conventional chemotherapy. Also, in the event that the instant adenoviral mutants elicit an immune response that dampens their effect in a host animal they can be administered with an appropriate immunosuppressive drug.

Propagation of Mutant Adenovirus

Adenoviral mutants of the invention typically are propagated as viral stocks in a cell line (e.g., the 293 cell line ATCC # CRL 1573, American Type Culture Collection, Rockville, Md.; Graham et al. (1977) *J. Gen. Virol.* 36: 59, or A549 cells) that can provide certain desired viral functions, if needed, in trans to support replication and formation of infectious mutant virions.

Formulations

Adenovirus E1B-55K mutants may be formulated for therapeutic and diagnostic administration to a patient. For therapeutic or prophylactic uses, a sterile composition containing a pharmacologically effective dosage of one or more species of adenovirus mutant is administered to a human patient or veterinary non-human patient for treatment, for example, of a neoplastic condition. Generally, the composition will comprise about $10^3$ to $10^{15}$ or more adenovirus particles in an aqueous suspension. A pharmaceutically acceptable carrier or excipient is often employed in such sterile compositions. A variety of aqueous solutions can be used, e.g., water, buffered water, 0.4% saline, 0.3% glycine and the like. These solutions are sterile and generally free of particulate matter other than the desired adenoviral virions. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. Excipients which enhance infection of cells by adenovirus may be included.

Adenoviruses of the invention, or the DNA contained therein, may be delivered to neoplastic cells by liposome or immunoliposome delivery; such delivery may be selectively targeted to neoplastic cells on the basis of a cell surface property present on the neoplastic cell population (e.g., the presence of a cell surface protein which binds an immunoglobulin in an immunoliposome). Typically, an aqueous suspension containing the virions are encapsulated in liposomes or immunoliposomes. For example, a suspension of adenovirus virions can be encapsulated in micelles to form immunoliposomes by conventional methods (U.S. Pat. Nos. 5,043,164, 4,957,735, 4,925,661; Connor and Huang (1985) *J. Cell*

Biol. 101: 582; Lasic D D (1992) Nature 355: 279; Novel Drug Delivery (eds. Prescott L F and Nimmo W S: Wiley, New York, 1989); Reddy et al. (1992) J. Immunol. 148: page 1585). Immunoliposomes comprising an antibody that binds specifically to a cancer cell antigen (e.g., CALLA, CEA) present on the cancer cells of the individual may be used to target virions, or virion DNA to those cells.

The compositions containing the present adenoviruses or cocktails thereof can be administered for prophylactic and/or therapeutic treatments of neoplastic disease. In therapeutic application, compositions are administered to a patient already affected by the particular neoplastic disease, in an amount sufficient to cure or at least partially arrest the condition and its complications. An amount adequate to accomplish this is defined as a "therapeutically effective dose" or "efficacious dose." Amounts effective for this use will depend upon the severity of the condition, the general state of the patient, the route of administration and the potency of the virus.

In prophylactic applications, compositions containing the invention adenoviruses, or cocktails thereof, are administered to a patient not presently in a neoplastic disease state to enhance the patient's resistance to recurrence of a neoplasm or to prolong remission time. Such an amount is defined to be a "prophylactically effective dose." In this use, the precise amounts again depend upon the patient's state of health and general level of immunity.

Single or multiple administrations of the compositions can be carried out with dose levels and pattern being selected by the treating physician. In any event, the pharmaceutical formulations should pro-vide a quantity of the antineoplastic adenoviruses of this invention sufficient to effectively treat the patient.

Antineoplastic adenoviral therapy of the present invention may be combined with other antineoplastic protocols, such as conventional chemotherapy. The preferred chemotherapeutics are cisplatin and 5-fluorouracil. Chemotherapy may be administered by methods well known to the skilled practitioner, including systemically, direct injection into the cancer, or by localization at the site of the cancer by associating the desired chemotherapeutic agent with an appropriate slow release material or intra-arterial perfusing the tumor.

The preferred chemotherapeutic agent is cisplatin, and the preferred dose may be chosen by the practitioner based on the nature of the cancer to be treated, and other factors routinely considered in administering cisplatin. Preferably, cisplatin will be administered intravenously at a dose of 50-120 mg/m$^2$ over 3-6 hours. More preferably it is administered intravenously at a dose of 80 mg/m$^2$ over 4 hours. Additionally, it is administered preferably on day 1 of treatment with adenovirus.

A second chemotherapeutic administration regime which is the combination of cisplatin with 5-fluorouracil. The preferred dose of 5-fluorouracil is 800-1200 mg/m$^2$ per day for 5 consecutive days (continuous infusion).

The Examples which follow are illustrative of specific embodiments of the invention, and various uses thereof. They are set forth for explanatory purposes only, and are not to be taken as limiting the invention.

EXAMPLE 1

Construction of E1B-55K Mutant Viruses

All E1B-55K mutants were generated using Stratagene's QuikChange™ Site-Directed Mutagenesis Kit following the manufacturer's recommended protocol. For each mutation, a forward primer and a reverse primer were used. The mutations and their respective primers are summarized in Table 2, below. Briefly, 20 ng of pXC-1 was used as the template and the cycling parameters were as follows: 1 cycle of 95° C. for 30 seconds, 16 cycles of 95° C. for 30 seconds, 55° C. for 1 minute and 68° C. for 20 minutes. The plasmid pXC-1 was obtained from Microbix Biosystems, Inc., located at 341 Bering Avenue, Toronto, Ontario Canada and contains the entire E1 region, E1A and E1B. The parental DNA was digested by adding 10 U of Dpn I to each sample and incubating for 1 h at 37° C. Final products were transformed into XL-1 cells (Stratagene Corp.), and confirmed by DNA sequencing.

Viruses were constructed by co-transfecting pJM17 with plasmids containing the mutations (Microbix Biosystems, Inc., located at 341 Bering Avenue, Toronto, Ontario Canada; McGrory, W. J., et al., Virology, 1988, vol. 163: p. 614-617) into 293 cells. Two rounds of plaque purification were done to rule out wild-type contamination. Mutations were confirmed by PCR followed by sequencing of the E1B-55K region. All viruses, including wild typeD, dl309 and ONYX-015, and the E1b-55K mutant viruses, were propagated in 293 cells, purified on CsCl gradients (as described in Adenovirus Methods and Protocols, edited by William S. M. Wold, 1999, Humana Press), and quantified by plaque assays and/or ELISA. The virus dl309 is described by Jones, N., and T. Shenk, Cell, 1979, vol. 17: p. 683-689.

TABLE 2

| Virus | Mutation | Primer sequences | SEQ ID NO: |
|---|---|---|---|
| ONYX-051 | R240A | GTTATTATGAATGTAGCGTTTACTGGCCCC | 1 |
| | | GGGGCCAGTAAACGCTACATTCATAATAAC | 2 |
| ONYX-052 | T255A | GTTTTCCTGGCCAATGCCAACCTTATCCTACAC | 3 |
| | | GTGTAGGATAAGGTTGGCATTGGCCAGGAAAAC | 4 |
| ONYX-053 | H260A | CCAACCTTATCCTAGCCGGTGTAAGCTTC | 5 |
| | | GAAGCTTACACCGGCTAGGATAAGGTTGG | 6 |
| ONYX-054 | C271A | GGGTTTAACAATACCGCCGTGGAAGCCTGG | 7 |
| | | CCAGGCTTCCACGGCGGTATTGTTAAACCC | 8 |
| ONYX-056 | R281A | CGATGTAAGGGTTGCGGGCTGTGCCTTTTAC | 9 |
| | | GTAAAAGGCACAGCCCGCAACCCTTACATCG | 10 |
| ONYX-057 | G282A | GTAAGGGTTCGGGCCTGTGCCTTTTAC | 11 |
| | | GTAAAAGGCACAGGCCCGAACCCTTAC | 12 |

TABLE 2-continued

| Virus | Mutation | Primer sequences | SEQ ID NO: |
|---|---|---|---|
| ONYX-058 | A284A | GTAAGGGTTCGGGGCTGTTCCTTTTACTGCTGCTGGAAGG | 13 |
| | | CCTTCCAGCAGCAGTAAAAGGAACAGCCCCGAACCCTTAC | 14 |
| ONYX-059 | F285L | GGTTCGGGGCTGTGCCTTATACTGCTGCTGGAAGGGG | 15 |
| | | CCCCTTCCAGCAGCAGTATAAGGCACAGCCCCGAACC | 16 |
| ONYX-060 | C288A | GGGCTGTGCCTTTTACTGCGCCTGGAAGGGGTGGTGTG | 17 |
| | | CACACCACCCCTTCCAGGCGCAGTAAAAGGCACAGCCC | 18 |
| ONYX-061 | W289F | GCTGTGCCTTTTACTGCTGCTTTAAGGGGGTGGTGTGTCGC | 19 |
| | | GCGACACACCACCCCCTTAAAGCAGCAGTAAAAGGCACAGC | 20 |
| ONYX-062 | W289A | GCTGTGCCTTTTACTGCTGCGCGAAGGGGTGGTGTGTCG | 21 |
| | | CGACACACCACCCCCTTCGCGCAGCAGTAAAAGGCACAGC | 22 |
| ONYX-063 | K290A | CTGCTGCTGGGCGGGGGTGGTG | 23 |
| | | CACCACCCCCGCCCAGCAGCAG | 24 |
| ONYX-064 | R295A | TGGAAGGGGGTGGTGTGTGCCCCCAAAAGCAGGGCTTC | 25 |
| | | GAAGCCCTGCTTTTGGGGGCACACACCACCCCCTTCCA | 26 |
| ONYX-065 | K297A | GGTGGTGTGTCGCCCCGCAAGCAGGGCTTCAATTAAGAAATG | 27 |
| | | CATTTCTTAATTGAAGCCCTGCTTGCGGGGCGACACACCACC | 28 |
| ONYX-066 | K303A | CCAAAAGCAGGGCTTCAATTGCGAAATGCCTCTTTGAAAGGTG | 29 |
| | | CACCTTTCAAAGAGGCATTTCGCAATTGAAGCCCTGCTTTTGG | 30 |
| ONYX-067 | E308A | CTTCAATTAAGAAATGCCTCTTTGCAAGGTGTACCTTGGGTATCC | 31 |
| | | GGATACCCAAGGTACACCTTGCAAAGAGGCATTCTTAATTGAAG | 32 |
| ONYX-068 | R309A | TCAATTAAGAAATGCCTCTTTGAAGCGTGTACCTTGGGTATCCTGTC | 33 |
| | | GACAGGATACCCAAGGTACACGCTTCAAAGAGGCATTTCTTAATTGA | 34 |
| ONYX-069 | E317A | TACCTTGGGTATCCTGTCTGCGGGTAACTCCAGGGTGCG | 35 |
| | | CGCACCCTGGAGTTACCCGCAGACAGGATACCCAAGGTA | 36 |
| ONYX-070 | G318A* | TACCTTGGGTATCCTGTCTGAGGCTACCTCCAGGGTCCGCC | 37 |
| | | GGCGGACCCTGGAGGTAGCCTCAGACAGGATACCCAAGGTA | 38 |
| ONYX-071 | G318A-N | TACCTTGGGTATCCTGTCTGAGGCTAACTCCAGGGTGCGCC | 39 |
| | | GGCGCACCCTGGAGTTAGCCTCAGACAGGATACCCAAGGTA | 40 |
| ONYX-080 | E421A | CTAAGATATTGCTTGAGCCGGCGAGCATGTCCAAGGTGAAC | 41 |
| | | GTTCACCTTGGACATGCTCGCCGGCTCAAGCAATATCTTAG | 42 |
| ONYX-081 | K425A | GAGCCCGAGAGCATGTCCGCGGTGAACCTGAACGGGG | 43 |
| | | CCCCGTTCAGGTTCACCGCGGACATGCTCTCGGGCTC | 44 |
| ONYX-082 | D433A | GAACCTGAACGGGGTGTTTGCCATGACCATGAAGATCTGG | 45 |
| | | CCAGATCTTCATGGTCATGGCAAACACCCCGTTCAGGTTC | 46 |
| ONYX-083 | K440A | CCATGAAGATCTGGGCGGTGCTGAGGTAC | 47 |
| | | GTACCTCAGCACCGCCCAGATCTTTCATGG | 48 |
| ONYX-084 | R443A | GGAAGGTGCTGGCGTACGATGAGACC | 49 |
| | | GGTCTCATCGTACGCCAGCACCTTCC | 50 |
| ONYX-085 | Y444A | GGAAGGTGCTGAGGGCCGATGAGACCCGC | 51 |
| | | GCGGGTCTCATCGGCCCTCAGCACCTTCC | 52 |

*Onyx-070 had two amino acids changed: Gly 318 to Ala, and Asn 319 to Thr.

EXAMPLE 2

Binding of E1B-55K Mutants with p53 and E4orf6

The twenty six mutant adenoviruses produced as described in Example 1 were initially screened to determine their effect on the steady-state levels of p53 in A549 cells. The rationale for conducting this experiment is that E1B-55K collaborates with E4orf6 to target p53 for active degradation. Thus, to identify E1B-55K mutants that lack this activity, we examined the steady-state level of p53 in infected A549 cells by Western blotting analysis (FIG. 1). Similar experiments were done with Onyx 015, wild type D (WtD) adenovirus, and dl309.

Western blotting analysis was carried out as follows. A549 cells were infected with various viruses at an MOI of 10. At 24 h post-infection, the cells were lysed in SDS gel loading buffer (100 mM Tris-Cl [pH 6.8], 5 mM EDTA, 1% SDS, 5% beta-mercaptoethanol). Proteins were fractionated by electrophoresis on Bio-Rad pre-cast protein gels. After electrophoresis, the proteins were electrophoretically transferred to nylon membranes. Blots were then incubated with antibodies diluted in PBS containing 1% dry milk and 0.1% Tween-20, and visualized by ECL (Amersham). Anti-p53 antibody DO-1 (Calbiochem) was diluted 1:1,000; anti-E1B-55K antibody 2A6 (Sarnow, P., et al., Cell, 1982, vol. 28: p. 387.) and anti-E2A antibody B6-6 (provided by Dr. Levine, Rockefeller University) were used as tissue culture supernatents, and diluted 1:10 before use. Anti-fiber antibody was diluted 1:1000.

FIG. 1 shows the results. In cells infected with dl309 or WtD, the p53 level was significantly reduced due to the targeted degradation mediated by E1B-55K and E4orf6. In contrast, cells infected with ONYX-015 exhibited an increase in p53 level. Most viral mutants caused a decrease in the level of p53. However, cells infected with the mutant E1B-55K viruses ONYX-051 and Onyx 053 (expressing E1B-55K mutants R240A and H260A, respectively) displayed a significant increase in p53 levels as compared to mock-infected A549 cells. All of the mutant adenoviruses accumulated E1B-55K protein to equivalent levels upon infection (FIG. 1). This observation suggest that two of the adenoviral E1B-55K mutants, R240A and H260A fail to bind p53 and/or E4orf6.

Figure 2:
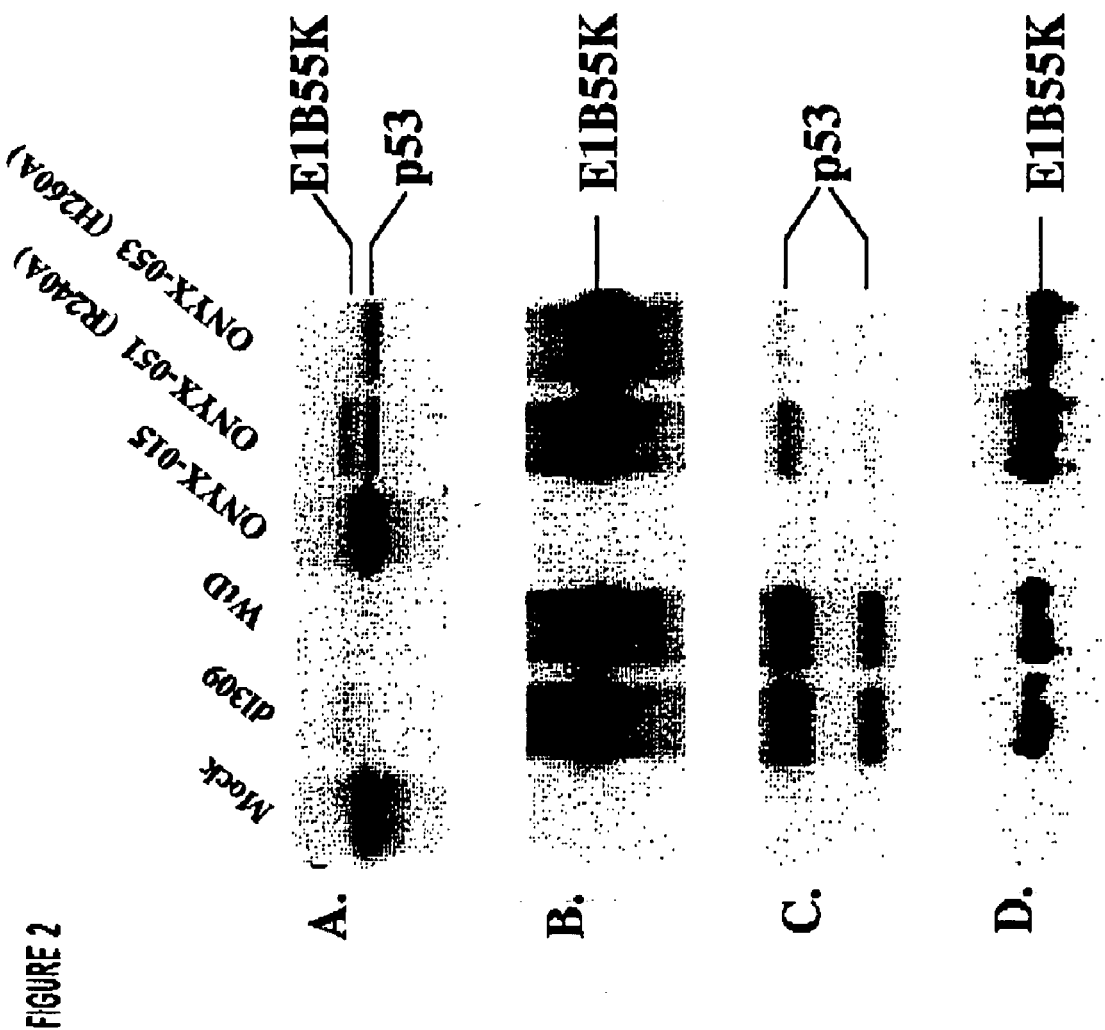
FIG. 2. Binding of p53 by E1B-55K mutants. (A and B). Co-immunoprecipitation experiment. A549 cells were either mock infected or infected with various virus mutants at an MOI of 10. At 24 hpi, cells were labeled with [35S] methionine-cysteine for a 3-h period. Cell extracts were immunoprecipitated with anti-p53 antibody Ab421 (A) or anti-E1B-55K antibody 2A6 (B), and analyzed by SDS-PAGE as described in Materials and Methods. E1B-55K mutant R240A was expressed from ONYX-051 and H260A was expressed from ONYX-053. (C and D). In-vitro binding experiment. p53 was synthesized and radioactively labeled with [35S] methionine by in vitro transcription and translation. Lysates were prepared from infected A549 cells at 24 hpi without radioactive labeling, incubated with radio-labeled p53, and immunoprecipitated with 2A6 antibody. The precipitated materials were separated by SDS-PAGE, and visualized either directly by autoradiography (C) or by Western blotting with 2A6 antibody (D).

This was confirmed by directly examining the ability of the E1B-55K mutants R240A and H260A to interact with p53 by immunoprecipitation experiments using $S^{35}$-labeled cell extracts from infected A549 cells (FIG. 2). These experiments were carried out as follows. A549 cells were infected at an MOI of 10 with the appropriate E1B-55K adenoviral mutant. At 24 h post-infection, cells were radio-labeled for 3 hours at 37° C. with methionine- and cysteine-free DMEM supplemented with 2% dialyzed fetal bovine serum and 100 uCi/ml of [35S]-express labeling mix (DuPont). Labeled cells were washed with cold saline, harvested and solubilized in 50 mM Tris-Cl (pH 8.0), 5 mM EDTA, 150 mM NaCl, 0.5% NP-40, 3 mM 2-mercaptoethanol, and 1×EDTA-free protease inhibitor mix (Boehringer Mannheim). Cells lysates were cleared by micro-centrifugation for 10 min. Immunoprecipitations were carried out as described previously (Shen, Y. and T. Shenk, Proc. Natl. Acad. Sci. USA, 1994, vol. 91: p. 8940-8944). Antibodies against p53 (mAb421) or E1B-55K (2A6) were used to bring down the protein complex. Proteins were separated by 4-20% SDS-PAGE gradient gel (Bio-Rad), and visualized by autoradiography.

The results are shown in FIGS. 2A and 2B. Anti-p53 antibody mAb421 co-precipitated small amount of wild-type E1B-55K protein from dl309 and WtD-infected cells, as expected (FIG. 2A). Both R240A and H260A mutant proteins were also co-precipitated, indicating they are capable of binding p53. Immunoprecipitation with the anti-E1B-55K antibody 2A6 brought down E1B-55K proteins (FIG. 2B), but it is hard to determine whether p53 was co-precipitated, as both proteins share similar molecular weights, and the E1B-55K protein was much more abundant. It is interesting to notice that the amounts of p53 in ONYX-051 and 053 infected cells as detected by immunoprecipitation were lower than in mock-infected cells, whereas in Western analysis, the p53 level is higher in ONYX-051 and 053 infected cells. This is due to the fact that Western blotting analysis detects the steady-state level of p53, whereas immunoprecipitation only detects newly synthesized p53. Thus, R240A and H260A were able to mediate host cell shut-off (see below), causing p53 to be synthesized at a lower rate than in mock-infected cells. The slow rate of synthesis for p53 and its higher steady-state level in cells that are infected with ONYX-051 and 053 again confirms that these viruses have lost their ability to target p53 for degradation.

An additional experiment was done to ensure that the differences in the levels of p53 in various cell extracts was not affecting the binding efficiency of the various E1B-55K mutant proteins to p53 from the co-immunoprecipitation experiment described above. Thus, in order to more accurately compare the binding efficiency of different E1B-55K mutant proteins to p53, we adopted an in vitro binding assay (Wienzek, S., et al., J. Virol., 2000, vol. 74: p. 193-202). Lysates of A549 cells infected with various adenoviruses were incubated with in-vitro [35S]-labeled p53, and the anti-E1B-55K antibody, 2A6, was used for immunoprecipitation. It is apparent from this experiment (FIG. 2C) that R240A and H260 bind p53 with significantly lower affinity than the wild-type E1B-55K protein. This inefficient precipitation of p53 was not due to lower level of mutant E1B-55K protein in cells infected with ONYX-051 or 053: Western analysis confirmed that similar or slightly higher level of E1B-55K was present in cell extracts derived from ONYX-051 and 053 infected cells (FIG. 2D). The inefficient binding of R240A and H260A to p53 may explain, at least in part, why p53 was not efficiently targeted for degradation in cells infected with ONYX-051 and 053.

In addition to the E1B-55K protein binding to p53, thus blocking p53-mediated transcription activation, E1B-55K collaborates with another adenovirus protein, E4orf6, to target p53 for active degradation in the cytoplasm. A further experiment was conducted to confirm the altered binding activity of the E1B-55K mutants to p53 by assessing their affects on relocating p53 to the cytoplasm. Thus, immunofluorescent staining of p53 and E1B-55K was conducted to determine whether the E1B-55K mutants R240A (Onyx 051) and H260A (Onyx 053) are able to relocate p53 to the cytoplasm (FIG. 3).

The experiment was conducted as follows. A549 and U2OS cells were seeded on Lab-Tek$^R$ II Chamber slides the day before infection to roughly 60% confluency. Cells were then infected at MOI of 10 with the following viruses: dl309, Onyx015, Onyx-051 (R240A), and Onyx-053 (H260A). Twenty four hours post infection, cells were washed with PBS and fixed for 30 min at room temperature using 4% formaldehyde in PBS. Cells were permeabilized and blocked with phosphate-buffered saline (PBS) supplemented with 0.1% Triton X-100, 0.05% Tween-20, and 10% goat serum for 30 minutes at room temperature, and then incubated for 1 hour at room temperature with properly diluted primary antibodies. All antibodies were diluted in the permeabilization/blocking solution. p53 antibody DO-1 (Calbiochem) was diluted 1:100; anti-E1B-55K antibody 9C10 (Calbiochem) was diluted 1:100, and a rabbit anti-E4orf6 antibody 1807-3 (a generous gift from Philip E. Branton) was diluted 1:500. Antigens were visualized with Alexa Fluor (red)-coupled secondary antibody (Molecular Probes).

Figure 3:
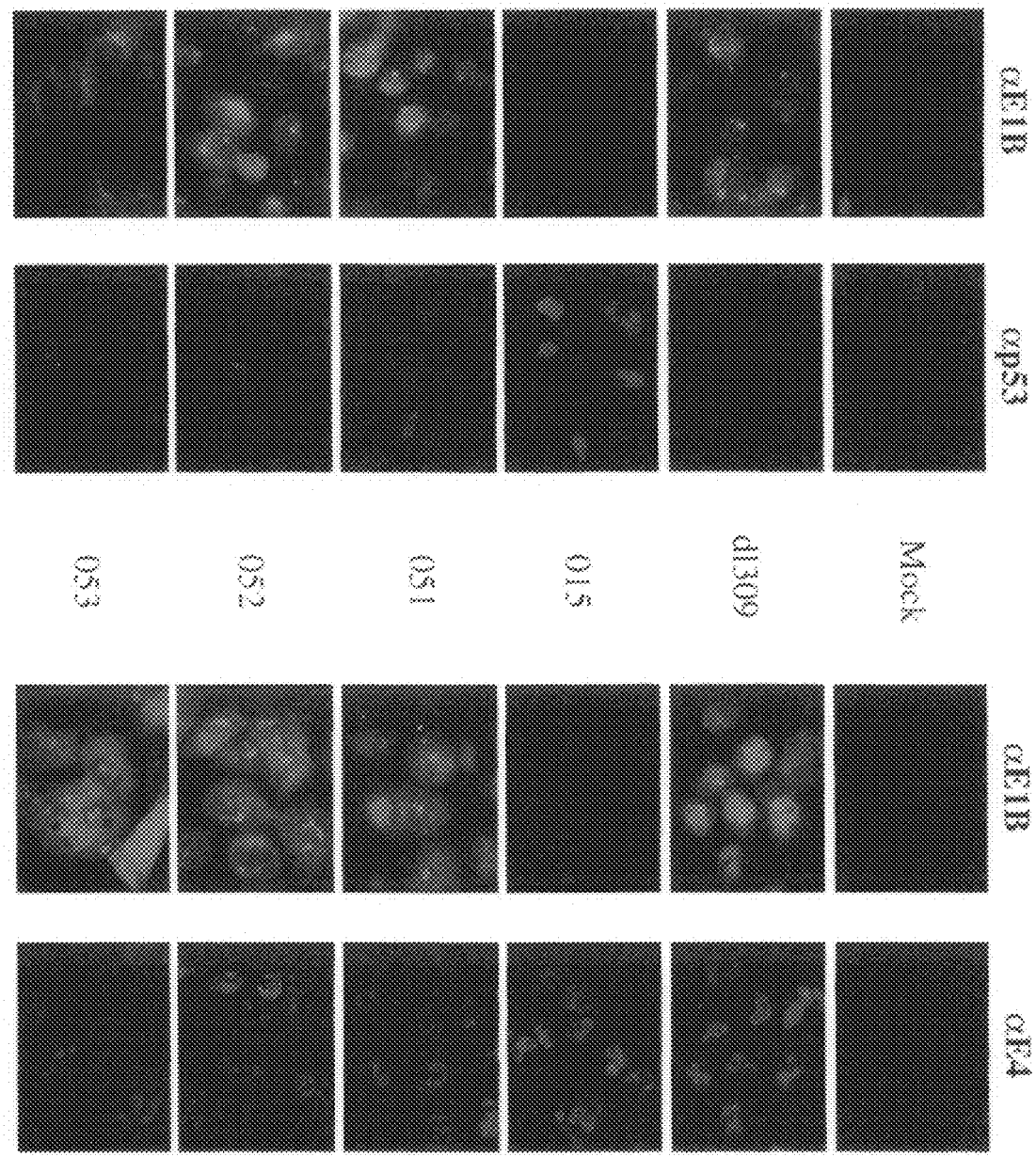
FIG. 3. Indirect immunofluorescent staining of adenovirus- and mock-infected cells. A549 cells grown on chamber slides were infected with dl309, ONYX-015, 051, 052 or 053 at an MOI of 10, or mock infected. At 24 h post-infection, the cells were fixed, permeabilized, and analyzed by indirect immunofluorescent staining using the E1B-55K specific monoclonal antibody 9C10 (alphaE1B), p53-specific monoclonal antibody DO-1 (alphap53), and E4orf6-specific polyclonal antibody 1807-3 (alphaE4). Representative fields are shown for all cases.

FIG. 3 shows the results. In mock infected A549 cells, p53 was detected exclusively in the nuclei. In cells infected with the wild-type virus dl309, p53 was present at a very low level, exclusively in the cytoplasm, and co-localized with the E1B-55K protein. Infection with ONYX-015 resulted in an elevated level of p53 localized in cell nuclei, as expected. In A549 cells infected with the R240A mutant virus (ONYX-051), p53 level was elevated (compare ONYX-051 and mock) in the nuclei, as in the case of ONYX-015 infection.

This is consistent with the fact that R240A binds p53 very weakly. In contrast, approximately two-thirds of the cells infected with ONYX-053 (H260A) had undetectable levels of p53, whereas the rest showed high levels of p53 in the nuclei. It is possible that this may reflect the cell cycle status of the cells when they were infected. In U2OS cells (which harbor wild-type p53), p53 was present at high levels in the nuclei when infected with ONYX-015, 051 and 053, but present in low levels when infected with dl309. These results further support the observation that the invention E1B-55K mutants ONYX-051, and ONYX-053 show substantially reduced binding of p53, and transport to the cytoplasm.

EXAMPLE 3

Effects of E1B-55K Mutations on Late Viral Functions

Cold Sensitivity. It is known that the replication of adenoviruses that have partial or complete deletion of the E1B-55K gene is temperature dependent (Leppard, K. N., J. Gen. Virol., 1993, vol. 74: p. 575-582; Goodrum, F. D and D. A. Ornelles, J. Virol., 1998, vol. 72: p. 9479-9490; and, Harada, J. N. and A. J. Berk, J. Virol., 1999, vol. 73: p. 5333-5344). At 39° C., they replicate nearly as well as the wild-type adenovirus. However, at 32° C., their replication is significantly reduced compared to the wild-type virus. This cold-sensitive phenotype of the E1B-55K defective viruses is interpreted to reflect the more severe defects in mRNA transport or late gene expression at the colder temperature (Goodrum, F. D. and D. A. Omelles, J. Virol., 1998, vol. 72: p. 9479-9490; and, Harada, J. N. and A. J. Berk, J. Virol., 1999, vol. 73: p. 5333-5344). To find out whether our E1B-55K mutants ONYX-051 (R240A) and ONYX-053 (H260A) can rescue the cold-sensitive phenotype, we performed the cold-sensitivity assay, using dl309 and ONYX-015 as controls (FIG. 4).

The cold sensitivity assay was conducted as follows. Infections of H1299 cells were performed at two temperatures, 32° C. and 39° C. Infections at 32° C. were perform d at 1 hour after the temperature shift from 39° C. All infections were at an MOI of 5. Infected cells were incubated at 32° C. and 39° C., respectively. At the indicated times, infected cells and culture media were harvested, pooled, and freeze-thawed 3 times to release virus particles. Viral yields were determined by ELISA on 293 cell monolayer.

Figure 4:
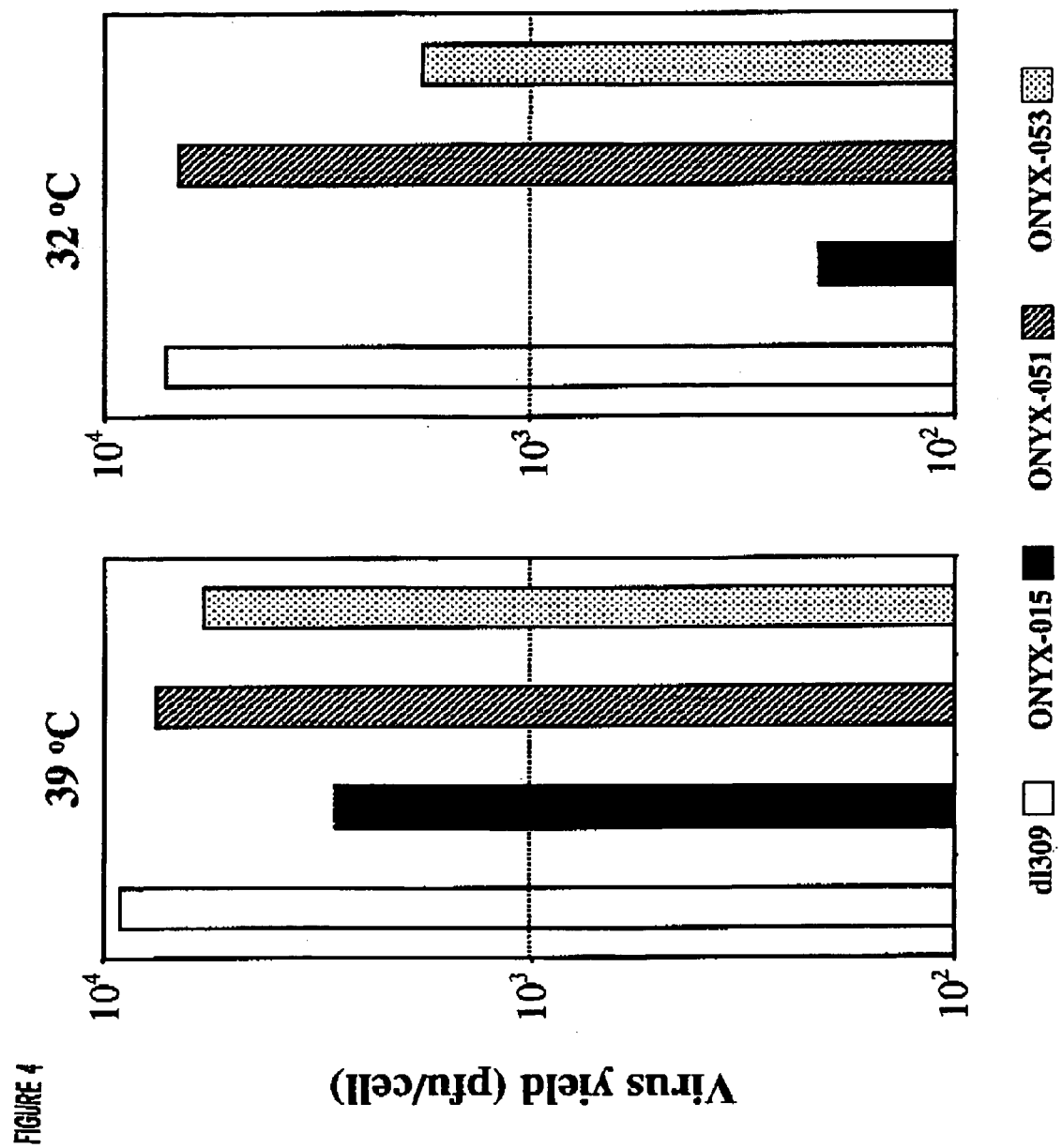
FIG. 4. Replication of dl309, ONYX-015, 051 and 053 as a function of time post-infection in p53-null H1299 cells at 32° C. and 39° C. H1299 cells were infected at two temperatures, 32° C. and 39° C. Infections at 32° C. were performed one hour after the temperature shift from 39° C. All infections were performed at an MOI of 5. Infected cells were incubated at 32° C. and 39° C., respectively. At the indicated times, infected cells and culture media were harvested, pooled, and freeze-thawed 3 times to release virus particles. Viral yields were determined by ELISA on 293 cell monolayer. Total viral yields were divided by the number of cells at the time of infection to determine viral production per cell. Results are the average from two independent experiments.

FIG. 4 shows the results. At 39° C., all viruses replicated to similar extent. The yield of dl309 was approximately 4-fold higher than that of ONYX-015, and the yields of ONYX-051 and ONYX-053 fell in between. At 32° C., however, the ONYX-015 yield was reduced nearly 35-fold compared to that of dl309, which is consistent with the previous reports. Replication of ONYX-051 was essentially identical to that of dl309, while replication of ONYX-053 was slightly reduced (4-fold). These results indicate that mutant R240A can completely rescue the cold-sensitive phenotype of the E1B-55K-defective adenovirus, whereas H260A does so substantially.

Total Protein Expression. An experiment was done to determine total protein expression during the late phase of viral infection. The rationale being that if the E1b-55K mutants that do not bind p53, but maintain late viral functions then such mutants, Onyx 051 and Onyx 053, should have a total protein expression pattern similar to dl309 or WtD. The protein expression pattern should also be distinguishable from Onyx 015, which does not bind p53, and lacks late viral functions.

The experiment was conducted as follows. A549 cells were either mock infected or infected with various adenovirus mutants, or Onyx 015, dl309 or WtD at an MOI of 10. At 24 h post-infection, cells were labeled with [35S] methionine-cysteine for a 3 hour period. Labeled cells were washed with cold saline, harvested and solubilized in 50 mM Tris-Cl (pH 8.0), 5 mM EDTA, 150 mM NaCl, 0.5% NP-40, 3 mM beta-mercaptoethanol, and 1×EDTA-free protease inhibitor mix (Boehringer Mennheim). Cleared cell extracts were resolved by SDS-PAGE (4-20%) and visualized by autoradiography.

Figure 5:
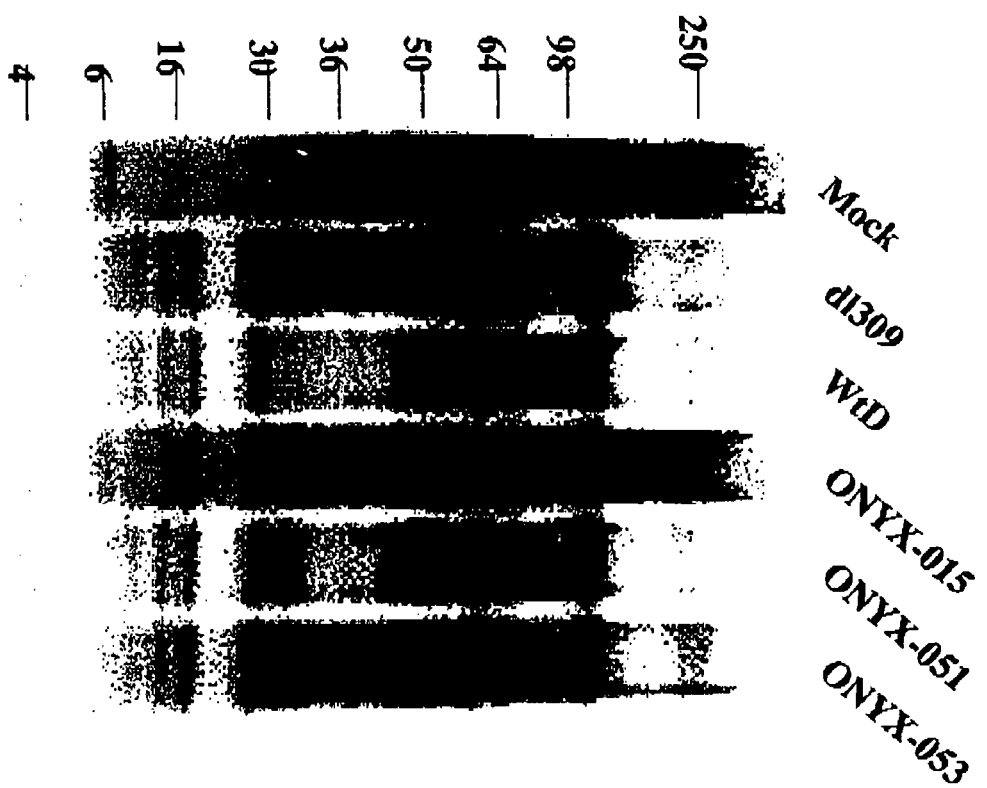
FIG. 5. Protein expression during the late phase of adenovirus infection. A549 cells were either mock infected or infected with various adenovirus mutants at an MOI of 10. At 24 h post-infection, cells were labeled with [35S] methionine-cysteine for a 3 hour period. Cell extracts were resolved by 4-20% SDS-PAGE gradient gel. The positions of the molecular mass markers are indicated at the left.

FIG. 5 shows the results. Expression of late viral proteins was efficient in dl309 and WtD infected cells, but poor in ONYX-015 infected cells. At the same time, de novo synthesis of the cellular proteins was reduced in cells infected with dl309 and WtD, compared to mock infection, due to host cell shutoff, but not in ONYX-015 infected cells. The protein synthesis profile in cells infected with ONYX-051 and 053 was similar to that in cells infected with wild-type viruses dl309 and WtD. This observation suggests that Onyx 051 (mutant R240A) and Onyx 053 (H260A) are capable of modulating mRNA trafficking in favor of late viral mRNA nuclear export.

Taken together, these results show that the E1B-55K mutants Onyx 051 (mutant R240A) and Onyx 053 (H260A) maintain the normal late functions of the wild-type protein.

EXAMPLE 4

Cytotoxic Activity of Adenoviral E1B-55K Mutants

Each E1B-55K mutant virus was tested for its ability to replicate in, and kill, the human tumor cell lines U2OS and DU145. The experiment was conducted as follows. An MTT assay was used in which the multiplicity of infection (MOI) at which 50% of the cells were killed was determined. DU145 and U2OS cells were seeded into 96-well plates at a density of $2.5 \times 10^3$ cells/well using DMEM-High Glucose supplemented with 2% FBS, 2 mM L-Glutamine, 100 ug/ml non-essential amino acids, 10 U/ml penicillin and 10 ug/ml streptomycin. The cells were infected twenty-four hours after seeding with the E1B-55K mutant viruses, or dl309 and ONYX-015. Infections started at an MOI of 30, with serial 3-fold dilutions. Infected cells were incubated at 37° C. and monitored daily. Incubation time was determined empirically. MTT assays were performed using Promega's CellTiter $96^R$ Non-Radioactive Cell Proliferation Assay according to the manufacturer's instructions.

Figure 6:
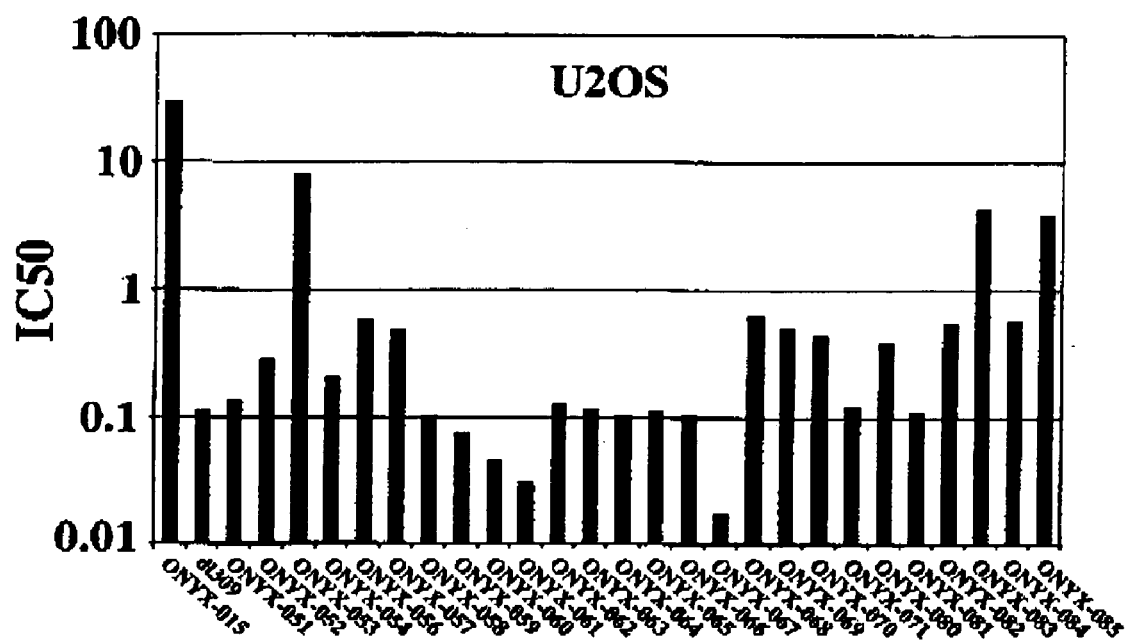
FIG. 6. Cytolytic activity in tumor cells. DU145 and U2OS cells were seeded into 96-well plates at a density of $2.5 \times 10^3$ cells/well using DMEM-High Glucose supplemented with 2% FBS, 2 mM L-Glutamine, 100 ug/ml none-essential amino acids, 10 U/ml penicillin and 10 ug/ml streptomycin. Twenty-four hours after seeding, cells were infected with serial 3-fold dilutions of E1B-55K mutant viruses, starting at an MOI of 30. dl309 and ONYX-015 were included as controls. The MOIs that killed 50% of the cells were defined as IC50, and were plotted for each virus.
Figure 6:
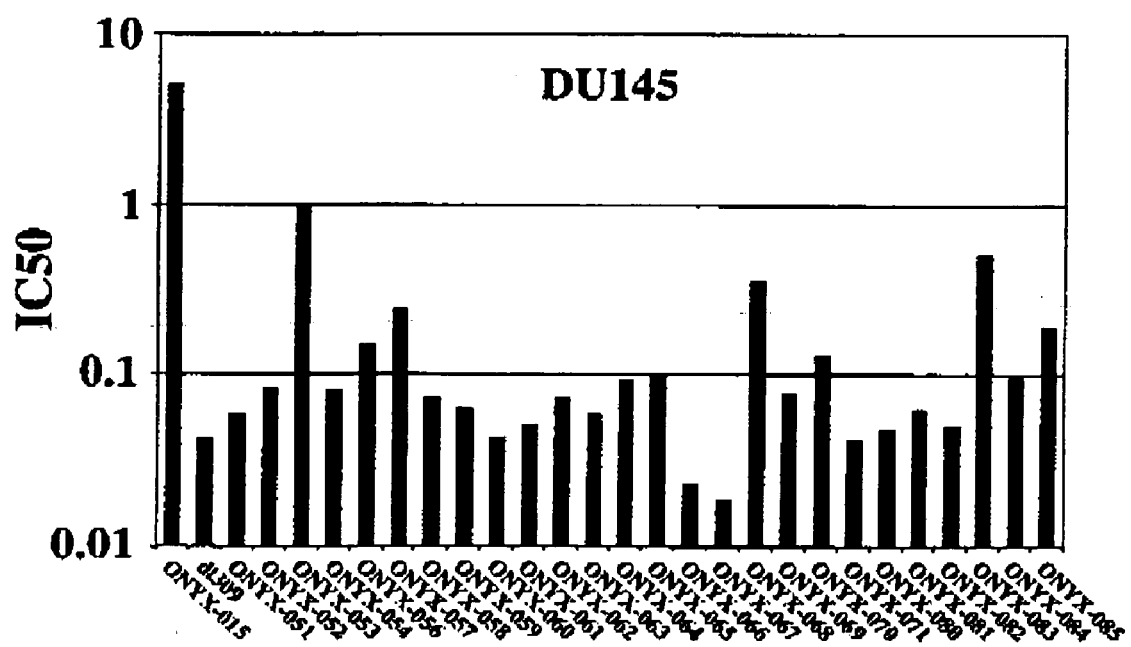

FIG. 6 shows the results. In both cell lines, ONYX-015 was severely attenuated as compared to its wild-type counterpart, dl309. Among the viruses that we created for this study, most, including ONYX-051, were comparable to dl309 in their ability to infect and kill tumor cells, though some, ONYX-053, 083 and 085, were significantly less potent than the wild-type virus, but more active than ONYX-015. In the case of ONYX-053, its tumor cytolytic activity was 35- to 100-fold lower than that of dl309, but more active than ONYX-015 by a factor of 4- to 5-fold.

Although the present invention has been described in some detail by way of illustration for purposes of clarity of understanding, it will be apparent that certain changes and modifications may be practiced within the scope of the claims.

The invention claimed is:

1. A method of treating a cancer, characterized by neoplastic cells that substantially lack p53 function, in a patient in need of the treatment, comprising administering chemotherapy to said patient, administering to said patient a dose of a recombinant adenovirus, said recombinant adenovirus comprising a mutation in the E1B-55K gene, said gene encoding a mutated E1B- 55K protein comprising a single amino acid substitution mutation, said single amino acid substitution mutation reducing the ability of said mutated E1B-55K protein to bind to the tumor suppressor p53 when compared to the ability of wild-type E1B-55K protein to bind to the tumor suppressor p53 and said recombinant adenovirus has the further property of retaining late viral function, and allowing sufficient time for said recombinant adenovirus to infect neoplastic cells of said cancer.

2. The method of claim 1, further comprising concomitantly administering said recombinant adenovirus with the chemotherapy.

3. The method of claim 1, wherein said adenovirus is Onyx 051 or Onyx 053.

4. The method of treating cancer of claim 3, wherein said recombinant adenovirus is Onyx 051.

5. The method of treating cancer of claim 3, wherein said recombinant adenovirus is Onyx 053.

6. The method of treating cancer of claim 1, wherein said treatment is repeated.

7. The method of treating cancer of claim 1, wherein said mutated E1B-55K protein comprises a single amino acid substitution mutation in amino acid 240 or 260.

8. The method of treating cancer of claim 1, wherein replication of said recombinant adenovirus is cold insensitive.

9. A method of treating a cancer, characterized by a tumor comprising neoplastic cells that substantially lack p53 function, in a patient in need of the treatment, comprising administering chemotherapy to said patient, administering by direct injection into the tumor a dose of a recombinant adenovirus, said recombinant adenovirus comprising a mutation in the E1B-55K gene, said gene encoding a mutated E1B-55K protein comprising a single amino acid substitution mutation, said single amino acid substitution mutation reducing the ability of said mutated E1B-55K protein to bind to the tumor suppressor p53 when compared to the ability of wild-type E1B-55K protein to bind to the tumor suppressor p53 and said recombinant adenovirus has the further property of retaining late viral function, and allowing sufficient time for said recombinant adenovirus to infect neoplastic cells of said cancer.

10. The method of claim 9, wherein said adenovirus is Onyx 051 or Onyx 053.

11. The method of treating cancer of claim 10, wherein said recombinant adenovirus is Onyx 051.

12. The method of treating cancer of claim 10, wherein said recombinant adenovirus is Onyx 053.

13. The method of treating cancer of claim 9, wherein said mutated E1B-55K protein comprises a single amino acid substitution mutation in amino acid 240 or 260.

14. The method of treating cancer of claim 9, wherein replication of said recombinant adenovirus is cold insensitive.

15. The method of treating cancer of claim 9, wherein said treatment is repeated.

* * * * *